US009796758B2

United States Patent
Melnyk et al.

(10) Patent No.: US 9,796,758 B2
(45) Date of Patent: Oct. 24, 2017

(54) NATIVE LIGATION PROCESS

(71) Applicants: CENTRE NATIONAL DE LA RECHERCHE SCIENTIFIQUE (CNRS), Paris (FR); INSTITUT PASTEUR DE LILLE, Lille (FR); UNIVERSITE LILLE 2 DROIT ET SANTE, Lille (FR)

(72) Inventors: Oleg Melnyk, Anoeullin (FR); Laurent Raibaut, Nice (FR); Nathalie Ollivier, Roubaix (FR)

(73) Assignees: CENTRE NATIONAL DE LA RECHERCHE SCIENTIFIQUE, Paris (FR); INSTITUT PASTEUR DE LILLE, Lille (FR); UNIVERSITE LILLE 2 DROIT ET SANTE, Lille (FR)

( * ) Notice: Subject to any disclaimer, the term of this patent is extended or adjusted under 35 U.S.C. 154(b) by 347 days.

(21) Appl. No.: 14/386,490

(22) PCT Filed: Mar. 18, 2013

(86) PCT No.: PCT/EP2013/055507
§ 371 (c)(1),
(2) Date: Sep. 19, 2014

(87) PCT Pub. No.: WO2013/139719
PCT Pub. Date: Sep. 26, 2013

(65) Prior Publication Data
US 2015/0045506 A1    Feb. 12, 2015

(30) Foreign Application Priority Data
Mar. 21, 2012 (FR) .................... 12 52548

(51) Int. Cl.
| | | |
|---|---|---|
| *C07K 7/08* | (2006.01) |
| *C07K 14/435* | (2006.01) |
| *C07D 293/02* | (2006.01) |
| *C08G 65/48* | (2006.01) |
| *C08F 20/56* | (2006.01) |
| *C08F 10/02* | (2006.01) |
| *C08G 63/91* | (2006.01) |
| *C08G 69/48* | (2006.01) |
| *C07K 7/06* | (2006.01) |
| *C08F 12/08* | (2006.01) |
| *C07K 1/02* | (2006.01) |
| *C07K 1/04* | (2006.01) |
| *C07K 1/08* | (2006.01) |
| *C07D 345/00* | (2006.01) |

(52) U.S. Cl.
CPC .............. *C07K 7/08* (2013.01); *C07D 293/02* (2013.01); *C07D 345/00* (2013.01); *C07K 1/026* (2013.01); *C07K 1/042* (2013.01); *C07K 1/088* (2013.01); *C07K 7/06* (2013.01); *C07K 14/435* (2013.01); *C08F 10/02* (2013.01); *C08F 12/08* (2013.01); *C08F 20/56* (2013.01); *C08G 63/91* (2013.01); *C08G 65/48* (2013.01); *C08G 69/48* (2013.01)

(58) Field of Classification Search
None
See application file for complete search history.

(56) References Cited

U.S. PATENT DOCUMENTS

2012/0220721 A1    8/2012  Melnyk et al.

FOREIGN PATENT DOCUMENTS

| WO | 9634878 A1 | 11/1996 |
| WO | 9828434 A1 | 7/1998 |
| WO | 0168565 A2 | 9/2001 |
| WO | 0187920 A2 | 11/2001 |
| WO | 2007037812 A1 | 4/2007 |
| WO | 2011051906 A1 | 5/2011 |

OTHER PUBLICATIONS

Huang et al., Chemical Communucations 47 (2011) 2408-2410.*
Ollivier et al., Organic Letters (2010) 12(22), 5238-5241).*
Quaderer et al., Helvetica Chimica Acta (2001) 84, 1197-1206).*
Ollivier et al., Organic Letters (2010) 12(22), 5238-5241.*
Muttenthaler, Markus, "Selenopeptide chemistry", Journal of Peptide Science, 2008, vol. 14, pp. 1223-1239.
International Search Report, dated Jun. 27, 2013, from corresponding PCT application.

* cited by examiner

*Primary Examiner* — Marcel M Cordero Garcia
*Assistant Examiner* — Catherine Mader
(74) *Attorney, Agent, or Firm* — Young & Thompson

(57) ABSTRACT

A method for producing a polypeptide, includes at least one native ligation step using a peptide functionalized with a selenium group. The selenium peptides and compounds are also described.

12 Claims, 25 Drawing Sheets

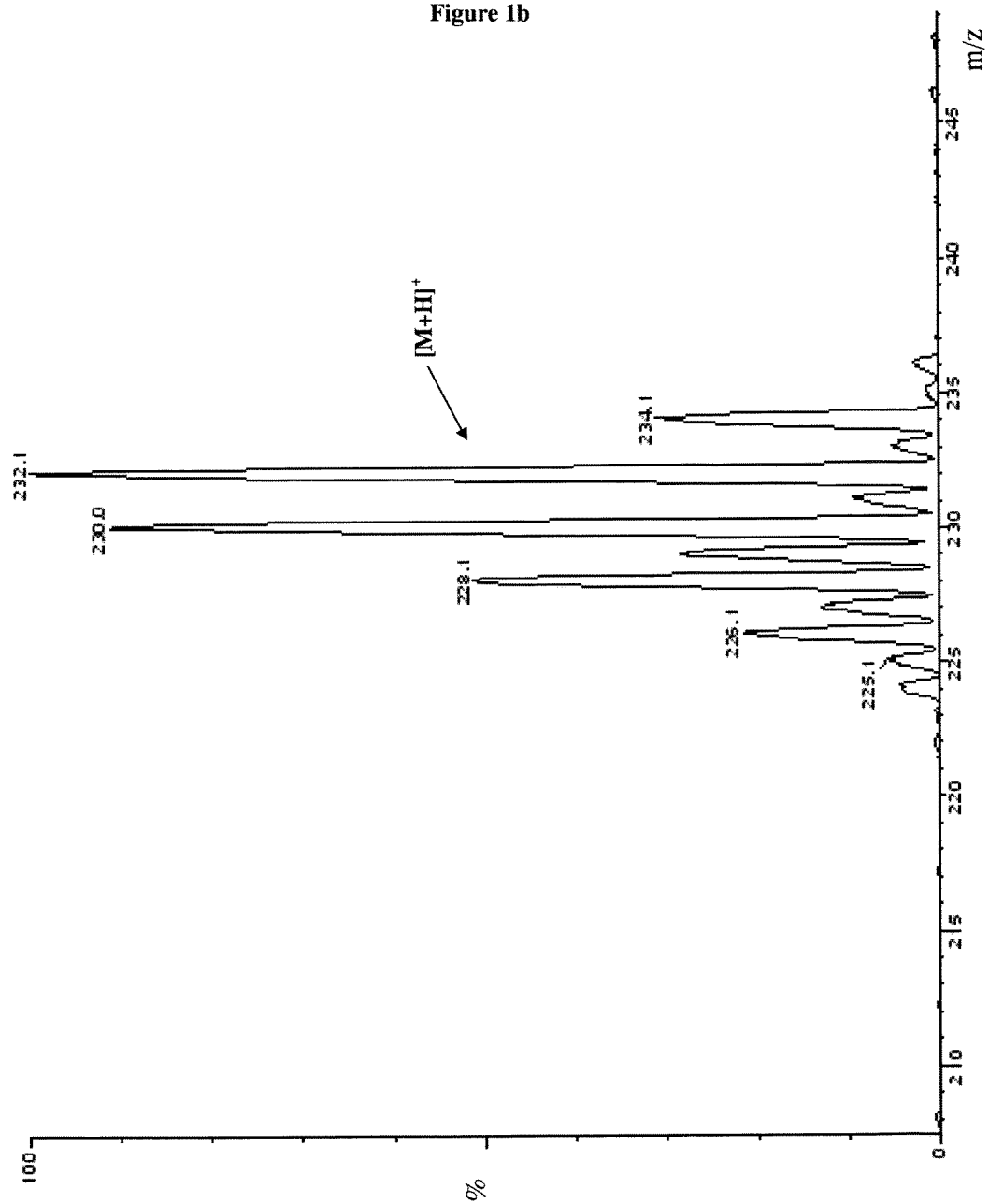

NATIVE LIGATION PROCESS

FIELD OF THE INVENTION

The present invention relates to a process for producing a polypeptide comprising at least one step of native ligation using a peptide functionalized by a selenium-containing group. The invention also relates to peptides and selenium-based compounds. The invention also relates to a synthesis kit for the synthesis of peptides.

TECHNOLOGICAL BACKGROUND

The synthesis of polypeptides by conventional solid-phase methods, amino acid by amino acid, is limited by low yields when the polypeptides synthesized are large. In order to overcome this limitation, it is known to assemble two polypeptides by chemical ligation in order to produce a longer polypeptide.

Total polypeptide synthesis is increasingly useful for preparing proteins with well-defined structures or bearing natural modifications, such as post-translational modifications, or unnatural modifications. Chemical ligation methods respond to this need; however they prove limited in their use and their industrial application.

Generally, in these methods, it is desirable for the link between the polypeptides assembled by ligation to be native, i.e. to correspond to the natural structure of the polypeptides.

The main native ligation method currently in existence is that of Kent and Dawson, described for example in international applications WO 96/34878 and WO 98/28434. This method is based on a chemoselective reaction between a (C-terminal) peptide thioester and a cysteinyl-peptide. Nevertheless, the main drawback of this method is the production of the peptide thioesters which require complex chemical processes. These methods of the prior art are unsatisfactory because they inevitably lead to mixtures that may be difficult to separate, thus affecting the purity of the end product obtained, and to inevitable losses in yield.

An alternative method is the ligation known as the Staudinger reaction, described in international applications WO 01/68565 and WO 01/87920. This comprises the reaction of a phosphinothioester with an azide and the hydrolysis of the combined reagents in order to form an amide bond. However this method is difficult to apply on an industrial scale.

Another method, described in international application WO 2007/037812, is based on the reaction of an α-ketoacid with an N-alkoxyamine in a decarboxylative condensation reaction. However, the ketoacids are molecules which are difficult to produce and incorporate into peptides. Also, this third method is difficult to apply in peptide synthesis laboratories that do not have the means to carry out complex organic syntheses.

The document WO 2011/051906 describes a native ligation process involving a thiol compound. Although this method is highly satisfactory, the reaction kinetics of this thiol compound are sometimes slow, in particular when the amino acids surrounding the bond between the two peptides are hindered.

A need therefore remained for a native ligation method provided with rapid reaction kinetics so as to facilitate the ligation of peptides by the formation of a bond between two hindered amino acids.

SUMMARY OF THE INVENTION

The invention is based on the development of a ligation method based on the use of a particular amide peptide, the SeEA peptide, and a cysteinyl peptide. When these two peptides are placed in contact in aqueous solution, a native peptide bond forms between the two fragments. The ligation is very efficient and takes place with excellent yields. It operates over a wide pH range.

This ligation has similarities with SEA ligation, described in the application FR 09 57 639, although there are significant differences between the properties of these two ligations and of the SeEA and SEA segments.

In fact, the kinetics of SeEA ligation are very significantly superior to the kinetics of SEA ligation, obtained with the sulphur-containing analogue SEA, or to the kinetics of Native Chemical Ligation (NCL) based on the use of peptide thioesters.

The kinetic superiority of SeEA does not in any way reduce the usefulness of SEA ligation. On the contrary, it complements it by allowing the formation of junctions that are difficult to produce by the other techniques of SEA ligation or NCL (thioester chemistry).

In the present application, the SEA group represents an —N(CH$_2$—CH$_2$—S-G$_4$)$_2$ group, with G$_4$ representing H or a sulphur protective group or a disulphide bond.

A first subject of the present invention relates to a functionalized peptide selected from:
a) the peptide of formula (I): X$_1$—N(CH$_2$CH$_2$SeH)$_2$; or
b) the peptide of formula (I'):

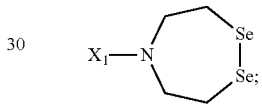

in which X$_1$ represents a peptide fragment and the —N(CH$_2$CH$_2$SeH)$_2$ group or

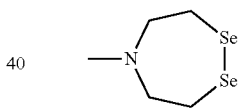

forms an amide bond with the C═O termination of the amino acid residue of the peptide fragment X$_1$ which is in the C-terminal position.

According to an embodiment, X$_1$ comprises from 2 to 300 amino acid residues, preferably from 5 to 100 amino acid residues, more particularly preferably from 8 to 50 amino acid residues.

Another subject of the present invention relates to a process for obtaining a functionalized peptide (I) or (I') according to the invention, comprising the following steps a1 and b1:
a1) peptide synthesis for providing a polypeptide of formula (II):

$$X_1\text{—OH} \qquad (II)$$

preferably comprising protective groups on its amine and carboxylic acid functions, with the exception of its C-terminal carboxylic acid function,
b1) functionalization of the polypeptide obtained in step a) comprising:
the reaction of the polypeptide of formula (II) with an amine compound selected from:

$$NH(CH_2\text{—}CH_2\text{—}Se\text{-}G_1)_2 \qquad (IIIa)$$

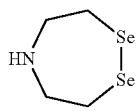

in which G₁ represents a selenium protective group or a hydrogen atom, in liquid phase, in order to form the polypeptide of formula (Ia) $X_1$—$N(CH_2CH_2$—$Se$-$G_1)_2$, or (I');

optionally the deprotection of the polypeptide of formula (Ia) in order to produce the compound of formula (I), or comprising the following steps a2 and b2:

a2) the use
   of the compound of formula (IV) or (IV"):

(IV)

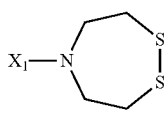

Or of a peptide functionalized by a group bearing a thio-ester function (IV')=$X_1$—SR and R represents an optionally substituted aryl or alkyl group, b2) the reaction between the compound of formula (IV) or (IV") or the compound of formula (IV') with the amine compound of formula (III') or (III"):

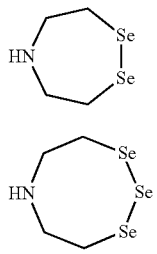

in liquid phase, in order to form the peptide of formula (I) or (I').

Another subject of the present invention relates to a compound capable of being used in the process for obtaining a functionalized peptide according to the invention, this compound being selected from:

a) the compound of formula (III'):

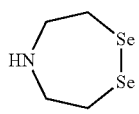

b) the compound of formula (III"):

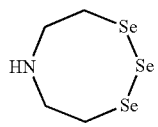

The invention also relates to a process for producing the compounds of formulae (III') and (III") according to the invention, comprising the following treatment reaction with a metal hydride illustrated in the diagram in the case of NaBH₄, but it is also possible to use LiAlH₄ or LiBH₄:

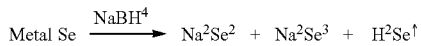

followed by the reaction:

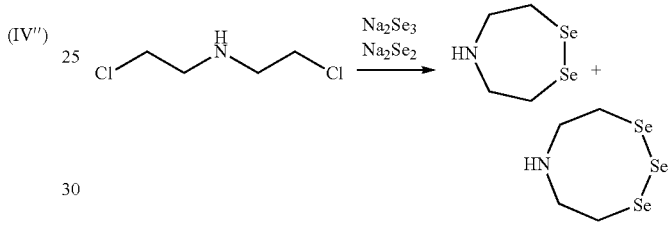

Another subject of the present invention relates to a process for obtaining a functionalized peptide (I) or (I') according to the invention, comprising the following steps:

a) Provision of a functionalized polymer resin with the structure (V):

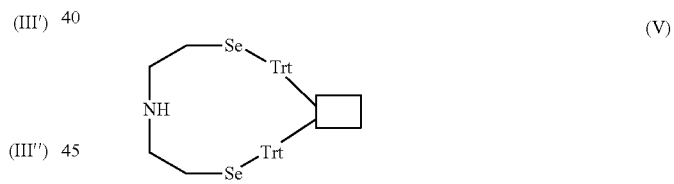

Or the structure (V'):

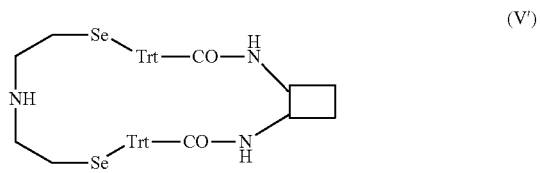

in which,
☐ represents a solid support,
Trt represents a triphenylmethyl group optionally substituted by one or more substituents, in particular selected from the substituents chlorine, methoxy, methyl, fluorine and cyano.

b) Grafting of an amino acid onto the functionalized polymer resin obtained in step a) in order to produce the compound of structure (VI):

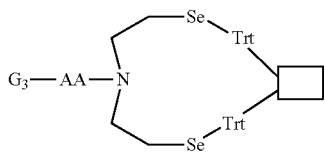

(VI)

Or of structure (VI'):

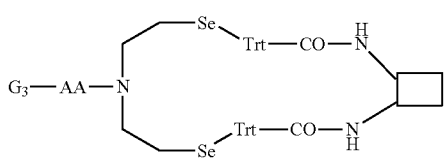

(VI')

in which,
  □ and Trt have the same meaning as in compound (V) or (V'),
  AA represents an amino acid residue optionally comprising one or more protective groups;
  $G_3$ represents a hydrogen atom or a protective group of the N-terminal amine function of AA,
c) Peptide synthesis starting from the amino acid AA in order to produce compound (VII) or (VII'):

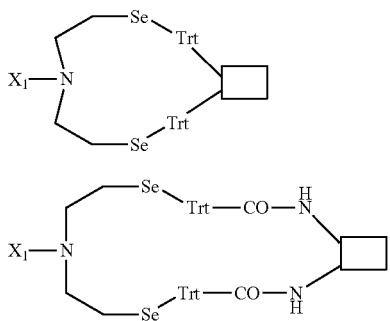

(VII)

(VII')

in which,
  □ represents a solid support,
  Trt represents a triphenylmethyl group optionally substituted by one or more substituents, in particular selected from the substituents chlorine, methoxy, methyl, fluorine and cyano,
  $X_1$ represents a peptide fragment,
d) Cleavage of the bond between Trt and Se in order to produce compound (I) or (I').

According to an embodiment of the process above, the grafting of an amino acid onto the polymer resin comprises bringing the functionalized resin (V) or (V') into contact with an amino acid halide or with an amino acid and an antivation agent, preferably selected from HATU, PyBOP, BOP, PyBROP, more particularly preferably HATU.

Another subject of the present invention relates to a functionalized polymer resin capable of being used in the process according to the invention, with the structure (V):

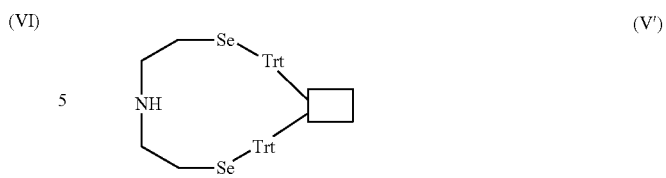

(V')

Or the structure (V'):

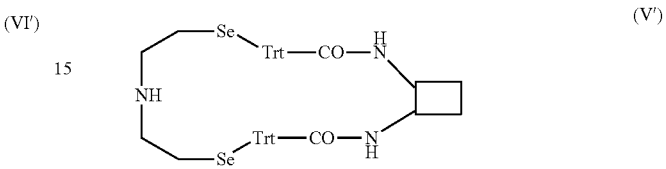

(V')

in which,
  □ represents a solid support,
  Trt represents a triphenylmethyl group optionally substituted by one or more substituents, in particular selected from the substituents chlorine, methoxy, methyl, fluorine and cyano.

Another subject of the present invention relates to a polymer resin comprising a peptide fragment corresponding to formula (VII) or (VII'):

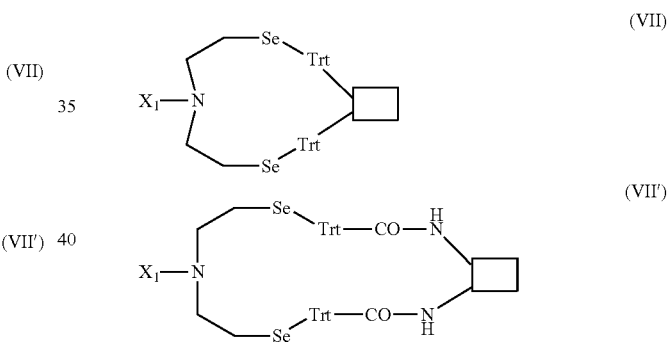

(VII)

(VII')

in which,
  □ represents a solid support,
  Trt represents a triphenylmethyl group optionally substituted by one or more substituents, in particular selected from the substituents chlorine, methoxy, methyl, fluorine and cyano,
  $X_1$ represents a peptide fragment.

According to an embodiment, the solid support □ is selected from a polystyrene, a polyacrylamide, a polyethylene glycol, a cellulose, a polyethylene, a polyester, a latex, a polyamide, a polydimethylacrylamide, a polyethylene glycol-polystyrene copolymer, a polyethylene glycol-polyacrylamide copolymer and derivatives thereof.

Another subject of the present invention relates to a process for producing the polymer resin according to the invention, comprising:
  a) the provision of a solid support functionalized by -Trt or —NH—CO-Trt groups;
  b) reaction of the Trt function of the solid support with the amine compound of formula (III): $NH(CH_2—CH_2—Se—H)_2$
  Trt having the same definition as above.

Another subject of the present invention relates to a process for producing a polypeptide of formula (VIII):

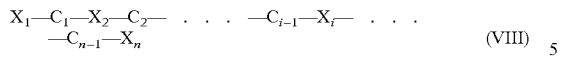  (VIII)

in which,
$X_1, X_2, \ldots, X_i, \ldots, X_n$ are peptide fragments,
$C_1, C_2, \ldots, C_{i-1}, C_{n-1}$ are amino acid residues bearing a thiol or selenol function,
n is an integer greater than or equal to 2,
i is any integer in the range from 1 to n,
this process comprising one or more steps of reaction between a compound of formula ($IX_i$):

  (IX$_i$)

in which,
$X'_1$ represents $X_1$
$X'_i$ represents $C_{i-1}$—$X_i$ for i>1
and a compound of formula ($X_{i+1}$):

  ($X_{i+1}$)

in order to form a compound of formula ($X_i$):

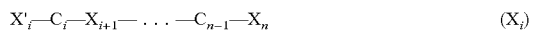  ($X_i$)

According to an embodiment, compound ($IX_i$) is formed from compound ($IX'_i$):

by bringing into contact with at least one compound that reduces diselenium bonds.

According to an embodiment, compound ($IX'_i$) is obtained by reaction between a compound of formula ($XI_i$), ($XI'_i$) or ($XI''_i$):

X'$_i$—S—R$_1$  (XI$_i$)

  (XI'$_i$)

X'$_i$—N(CH$_2$—CH$_2$—S—H)$_2$  (XI''$_i$)

in which X'$_i$ is a peptide fragment of the form $C_{i-1}$—$X_i$ for i>1 and X'$_i$ represents $X_1$, $R_1$ represents an optionally substituted alkyl or aryl group, and a compound of formula (III') or of formula (III'') according to the invention.

According to an embodiment, the process above is implemented for the production of a polypeptide represented by formula (XII):

$X_1$—$C_1$—$X_2$—$C_2$—$X_3$  (XII)

comprising the following steps:
a) reaction between a compound of formula (XIII) or (XIII'):

$R_2$—$X_1$—N(CH$_2$—CH$_2$—Se—H)$_2$  (XIII)

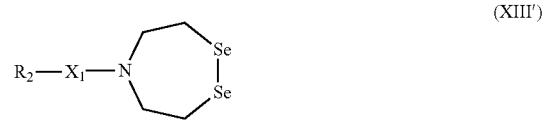  (XIII')

and a compound of formula (XIV) or (XIV'):

H—$C_1$—$X_2$—N(CH$_2$—CH$_2$—S—H)$_2$  (XIV)

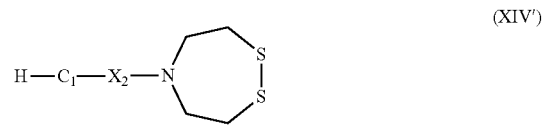  (XIV')

in order to form the compound of formula (XV) or (XV'):

$R_2$—$X_1$—$C_1$—$X_2$—N(CH$_2$—CH$_2$—S—H)$_2$  (XV)

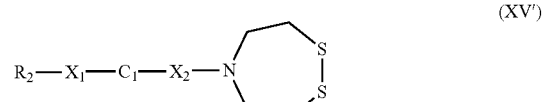  (XV')

b) reaction between a compound of formula (XV) or (XV') and a polypeptide of formula (XVI):

H—$C_2$—$X_3$  (XVI)

in order to form the compound of formula (XII),
in which, $R_2$ represents H or a protective group of the N-terminal function of $X_1$; $X_1$, $X_2$, $X_3$ represent, independently of each other, peptide fragments; $C_1$ and $C_2$ represent, independently of each other, amino acid residues bearing a thiol or selenol function.

Another subject of the present invention relates to a process for producing a cyclic polypeptide of formula (XVII):

  (XVII)

$X_2$ representing a peptide fragment, and $C_1$ representing an amino acid residue comprising a thiol or selenol function,
said process comprising at least one reaction step of ligation of a polypeptide of formula (XVIII):

H—$C_1$—$X_2$—N(CH$_2$—CH$_2$—Se—H)$_2$  (XVIII)

with itself.

According to an embodiment of the process for producing a cyclic polypeptide according to the invention, the ligation reaction is carried out by placing a polypeptide of formula (XVIII'):

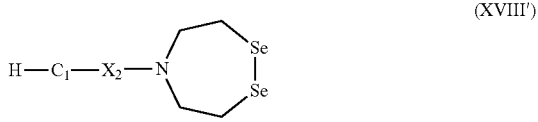

(XVIII')

in contact with at least one compound that reduces diselenium bonds.

Another subject of the present invention relates to a polypeptide synthesis kit comprising one or more peptides of formulae (IX$_i$) or (IX'$_i$) capable of being used in the ligation process according to the invention, or at least one compound (III') or (III") according to the invention.

Advantages of the present invention are the following:
- the native ligation of the invention makes it possible to achieve the binding of difficult junctions, such as hindered junctions,
- the kinetics of native ligation of the invention are very rapid,
- the native ligation of the invention can be combined with other ligation methods having different kinetics,
- the native ligation of the invention is simple to implement,
- the SeEA peptides can be produced from a solid support,
- The SeEA peptides can be produced from SEA segments or thioester in solution
- the native ligation of the invention can be implemented starting from peptide fragments which can be prepared in solid phase or in liquid phase,
- the native ligation of the invention can be combined with other types of native ligations of the prior art in a one-pot process comprising several successive ligations,
- the native ligation of the invention can be carried out by implementing a ligation process of the prior art by the simple addition of a particular selenium-containing compound to the reaction mixture.

BRIEF DESCRIPTION OF THE FIGURES

Other features and advantages of the invention will become apparent on reading the following description of a preferred embodiment of the invention, given by way of example and with reference to the attached drawings.

FIGS. 1a and 1b represent respectively the HPLC chromatogram and the mass spectrum of a selenium-containing compound according to the invention.

DESCRIPTION OF EMBODIMENTS OF THE INVENTION

Figure 1A:
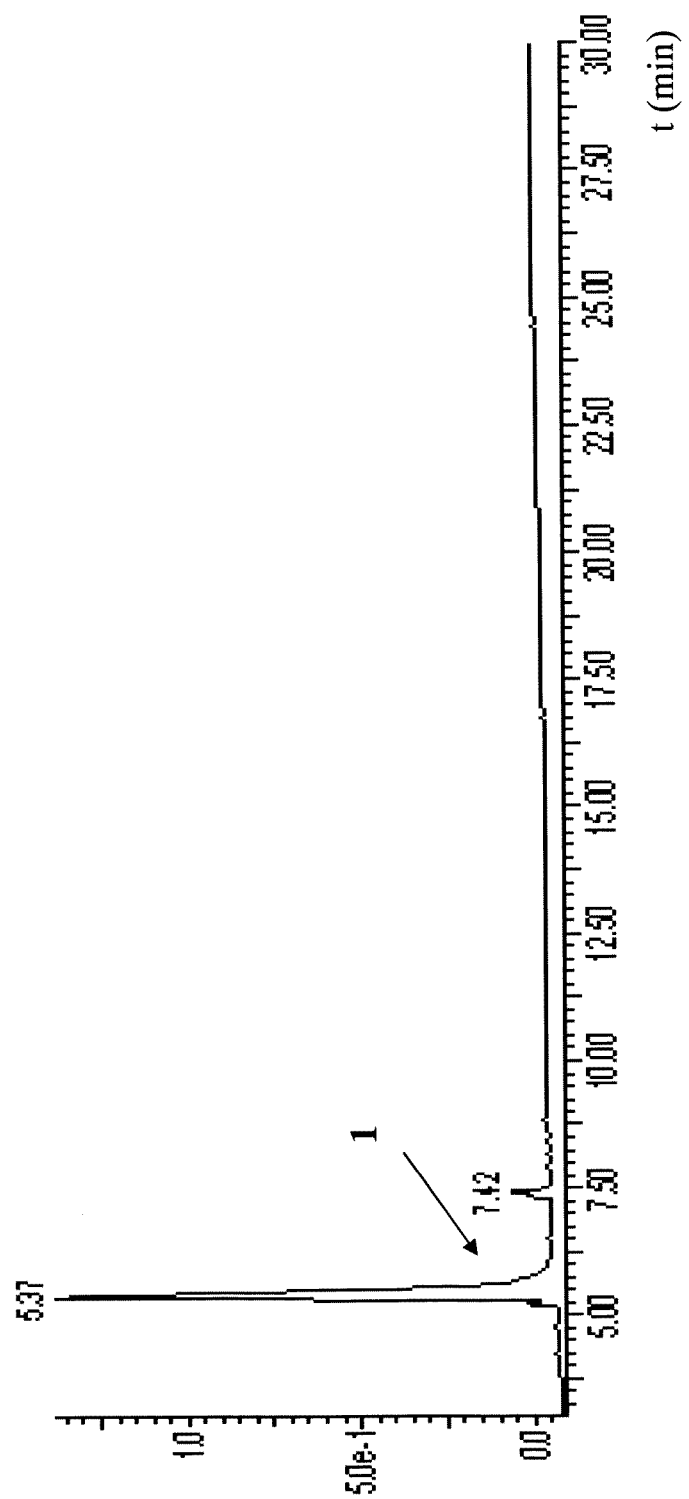

The invention is now described in more detail and non-limitatively in the following description.

By "peptide or polypeptide" is meant, in the context of the present application, a linear chain of amino acid residues (of a number greater than or equal to two) linked by peptide bonds. The "peptides or polypeptides" within the meaning of the present application can therefore for example be oligopeptides, peptides or proteins according to the conventional acceptance of these terms. The amino acid residues present in the polypeptides according to the invention can be selected from the proteinogenic or non-proteinogenic amino acid residues. Preferably, they are selected from the twenty proteinogenic amino acid residues and selenocysteine.

The polypeptide notation is carried out from the N-terminal end towards the C-terminal end. The usual one-letter or three-letter code is used for notation of the amino acid residues present along the polypeptide chain. An amino acid residue is a polypeptide fragment of formula —NH—(CH—R)—(C=O)—, in which R represents a side chain, which differs from one amino acid to another.

By "peptide fragment" is meant, in the context of the present application, a portion of polypeptide comprising at least one amino acid residue. A peptide fragment, within the meaning of the present application, can therefore be for example: a sequence of amino acid residues (such as -AHG- or -Ala-His-Gly-) if the peptide fragment comprises neither the N-terminal end nor the C-terminal end of the polypeptide; or a sequence of amino acid residues with a group at its N-terminal end (such as H-AHG- or H-Ala-His-Gly-) if the peptide fragment comprises the N-terminal end of the polypeptide; or a sequence of amino acid residues with a group at its C-terminal end (such as -AHG-OH or -Ala-His-Gly-OH) if the peptide fragment comprises the C-terminal end of the polypeptide.

Functionalized Peptide

A first subject of the invention relates to a peptide functionalized by a selenium group selected from:
a) the peptide of formula (I): $X_1$—N(CH$_2$CH$_2$SeH)$_2$;
b) the peptide of formula (I'):

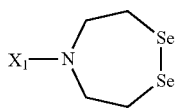

in which $X_1$ represents a peptide fragment and the —N(CH$_2$CH$_2$SeH)$_2$ group or

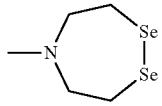

forms an amide bond with the C=O termination of the amino acid residue of the peptide fragment $X_1$ which is in the C-terminal position.

The peptide fragment $X_1$ is in the form $Y_1$-AA$_1$-AA$_2$-...-AA$_n$ in which $Y_1$ is an N-terminal group, preferably a hydrogen atom, but optionally also any group being substituted for the primary or secondary amines known to a person skilled in the art, for example an acyl group and in particular an acetyl group; n is an integer greater than or equal to 2; AA$_1$, AA$_2$, ..., AA$_n$ represent, independently of each other, amino acid residues.

The polypeptide of formula (I) or (I') preferably comprises from 2 to 300 amino acid residues, preferably from 5 to 100 amino acid residues, more particularly preferably from 8 to 50 amino acid residues.

The polypeptides of formula (I) or (I') preferably comprise only amino acid residues selected from the twenty proteinogenic amino acid residues and selenocysteine. However, according to a particular embodiment, the polypeptides of formula (I) or (I') comprise one or more non-proteinogenic amino acid residues.

The amino acid residues of the polypeptides of formula (I) or (I') can optionally be protected by side chain protective groups.

Amine Compound of Formula (III') and (III")

Another subject of the invention relates to the amine compounds of formula (III') and (III") below and their production process.

Compounds (III') and (III") correspond to the formulae:

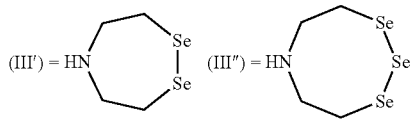

Compounds (III') and (III") can be obtained according to the process comprising the following step a):

followed by the following step b):

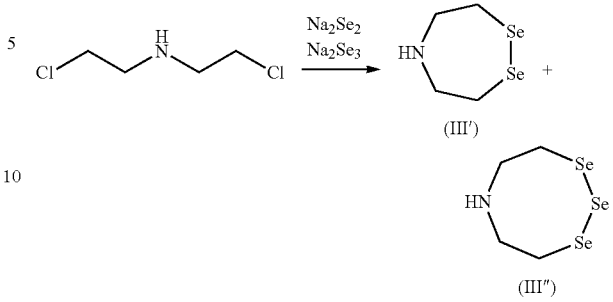

The first step above (step a) is preferably carried out under a nitrogen atmosphere. Preferably, the reagents are introduced cold, then the mixture is taken to reflux.

According to another embodiment, in step a), NaBH$_4$ is replaced with another metal hydride, such as LiAlH$_4$ or LiBH$_4$. In the case of the two metal hydrides mentioned, the compounds Li$_2$Se$_2$ and Li$_2$Se$_3$ are formed. These two compounds Li$_2$Se$_2$ and Li$_2$Se$_3$ are then used in the following step b).

Preferably, the second step (step b) is carried out at ambient temperature.

Preferably, the organic phase comprising the products (III') and (III") is purified at the end of the process, for example, by high performance liquid chromatography.

Process for Obtaining Compounds (I) and (I') in Liquid Phase

Another subject of the invention relates to a process for obtaining the functionalized polypeptide (I) or (I') in liquid phase, this process comprises a first step of peptide synthesis and a second step of functionalization.

The first step (peptide synthesis step) makes it possible to obtain the polypeptide of formula:

$$X_1-OH \qquad (II)$$

This peptide synthesis step can be carried out according to any method known to a person skilled in the art. It can in particular be carried out in liquid phase or, preferably, in solid phase.

In principle, peptide synthesis comprises a succession of couplings of amino acids starting from a primer (initial amino acid or peptide fragment resulting from the preceding amino acid additions) and from deprotections. More precisely, the peptide synthesis can successively comprise:

(a) the provision of a peptide fragment with an unprotected N-terminal end, and of an amino acid protected at its N-terminal end;

(b) the establishment of a peptide bond between the amino acid and the peptide fragment, at the N-terminal end of said peptide fragment;

(c) the deprotection of the N-terminal end of the linked amino acid, in order to provide the peptide fragment of the following step (a).

During the different coupling reactions, it is advantageous to use an activator compound, in particular a carbodiimide (for example dicyclohexylcarbodiimide or diisopropylcarbodiimide) in the presence of a triazole (for example 1-hydroxy-benzotriazole or 1-hydroxy-7-azabenzotriazole), or a phosphonium or uronium salt of a non-nucleophilic anion (for example HBTU, HATU, TBTU or PyBOP); or also to use activated amino acids in the form of acid halides, for example acid fluorides.

During the different coupling reactions, the N-terminal ends of the amino acids are advantageously protected by a protective group, preferably a Fmoc group (9H-fluoren-9-ylmethoxycarbonyl) or also a t-Boc group (tert-butoxycarbonyl) or NSC group (2-(4-nitrophenylsulphonyl)ethoxycarbonyl).

Similarly, the side chains of the amino acid residues are preferably protected during the different coupling reactions by one or more appropriate protective groups, for example a tert-butyl group for the chains bearing a carboxylic acid function.

In this case, once the last amino acid coupling reaction has been carried out, a deprotection reaction of the side chains can be provided. It should however be noted that it may be preferable to retain all of the protections (with the exception of an optional protection of the COOH function at the C-terminal end) for the functionalization step.

Functionalization

The functionalization step comprises successively:

Optionally, the protection of the N-terminal end of the polypeptide of formula (II) with a protective group, preferably selected from the family of the carbamates, amides or alkyl groups, and in particular a tert-butoxycarbonyl group (t-Boc), Fmoc (9H-fluoren-9-ylmethoxycarbonyl), trifluoroacetyl or triphenylmethyl.

Optionally also, the protection of the functions of the side chains of the amino acid residues of the polypeptide of formula (II), and quite particularly of the amine functions (preferably by means of the protective groups above) and carboxylic acid functions (by means for example of tert-butyl groups).

Alternatively, and according to a simpler embodiment, it is possible to provide the polypeptide of formula (II) directly in a form in which all of the amine and carboxylic acid functions are protected, by providing selective deprotection of the COOH function of the C-terminal end.

The liquid phase coupling reaction of the polypeptide of formula (II) with an amine compound selected from compounds (IIIa) and (III') where:

(IIIa)

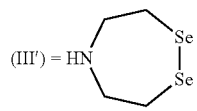

in which $G_1$ represents a selenium-protective group,

Optionally the deprotection of the polypeptide.

According to an embodiment, the protective group $G_1$ of compound (IIIa) is selected from the groups of triphenylmethyl and benzyl type and in particular from para-methylbenzyl or para-methoxybenzyl.

In the case where compound (IIIa) is used as starting reagent for coupling with compound (II), a subsequent step of deprotection of the group $G_1$ is provided in order to obtain compound (I) or (I'). Preferably, the deprotection is carried out by treatment with an acid such as trifluoroacetic acid or hydrofluoric acid, or an oxidant such as iodine.

An activator is advantageously present during the coupling reaction, for example benzotriazol-1-yl-oxytripyrrolidinophosphonium hexafluorophosphate (PyBOP) or bromo-trispyrrolidinophosphonium hexafluorophosphate (PyBROP) or the C-terminal amino acid itself is activated in the form of a halogenated derivative (in particular in the form of an amino acid fluoride or amino acid chloride), the latter being able to be pre-formed or formed in situ using appropriate reagents known to a person skilled in the art. Among the amino acid halides, the amino acid fluorides are preferred, pre-formed by reaction with 1,3,5-trifluorotriazine or formed in situ using TFFH (tetramethylfluoroformamidinium hexafluorophosphate).

Generally, it is also possible to envisage any reagent allowing the activation of the carboxylic acid function of the amino acid known to a person skilled in the art such as HBTU, TBTU, HATU, BOP etc. (reference may be made for example to *Chemical approaches to the synthesis of peptides and proteins* by Lloyd-Williams, P., Albericio, F., Giralt, E., 1997, CRC Press). PyBOP, PyBROP, BOP (benzotriazole-1-yl-oxy-tris-(dimethylamino)-phosphonium) hexafluorophosphate or more generally the phosphoniums are preferred.

The functionalized polypeptide (I) or (I') according to the invention can be obtained according to a second variant.

The SeEA segments can be formed separately by exchange starting from an SEA segment of $X_1$—N($CH_2CH_2$—S-$G_4$)$_2$ or $X_1$—S—$R_1$ thioester type using the reagents of structure (III') or (III"), $G_4$ representing a hydrogen atom, a thiol function protective group or a disulphide bond and $R_1$ representing a hydrogen atom or an optionally substituted alkyl or aryl group.

The SeEA segments can also be formed in situ, during the exchange ligation starting from an SEA segment of $X_1$-SEA or $X_1$—$SR_1$ thioester type using reagents (III') or (III"). The segment of H-Cys-$X_2$ type present in solution consumes the $X_1$-SeEA segment formed by the exchange. In general, the $X_1$-SeEA segment formed in situ is not observed since it reacts very rapidly with the H-Cys-$X_2$ segment. Due to the rapidity of the exchange and of the SeEA ligation, this results in a very significant acceleration of the ligation, once the reagent (III') or (III") is introduced into the ligation reaction medium.

Thus, according to a second variant, compounds (I) and (I') are obtained by the following successive steps:

a2) the provision of a peptide functionalized on its C-terminal end by a group bearing a thiol function corresponding to formula (IV) or (IV"):

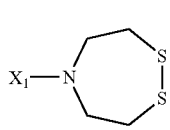

(IV")

of a peptide functionalized by a group bearing a thioester function (IV') =$X_1$—SR and R represents an optionally substituted aryl or alkyl group, b2) the liquid-phase reaction between the compound of formula (IV) or the compound of formula (IV") or the compound of formula (IV') and an amine compound of formula (III') or (III"):

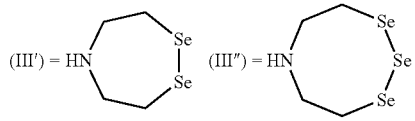

optionally in the presence of a compound that reduces the disulphide bond in the case where compound (IV″) is used.

The compound of formula (IV) or of formula (IV″) can in particular be obtained according to the protocol described in the document WO 2011/051906.

In formula (IV'), the R group preferably represents an optionally substituted C1-C12 alkyl or an optionally substituted C6-C12 aryl. Such compounds are described in particular by WO96/34878 and WO98/28434.

According to an embodiment, the compound that reduces the disulphide bonds can be selected from the thiol compounds, such as 4-mercaptophenylacetic acid (MPAA), dithiothreitol (DTT), thiophenol and its derivatives, an alkylthiol (in particular benzylmercaptan), from the selenol compounds such as selenophenol or diphenyl selenide or from the phosphines such as tris(2-carboxyethyl)phosphine (TCEP), or mixtures thereof.

At the end of the previous coupling reaction, compound (I') is obtained. Compound (I) is obtained by placing compound (I') in contact with a compound that reduces diselenium or triselenium bonds.

Among the known compounds that reduce diselenium or triselenium bonds, there may be mentioned: tris(2-carboxyethyl)phosphine (TCEP), the reducing thiols such as 4-mercaptophenylacetic acid (MPAA), thiophenol, benzylmercaptan, dithiothreitol (DTT), selenophenol or diphenyl selenide plus a diselenium bond reducing agent, metallic zinc, and hydrides such as $NaBH_4$, $LiBH_4$, $NaBH_3CN$, $NaBH(OAc)_3$.

At the end of the functionalization step, the polypeptide of formula (I) or (I') is obtained. It is advantageous to provide at this step a compound purification step, for example by liquid chromatography.

Functionalized Polymer Resin

Another subject of the invention relates to the functionalized polymer resins corresponding to structure (V) or (V'):

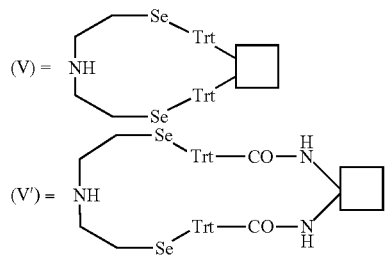

in which,
☐ represents a solid support,
Trt represents a triphenylmethyl group optionally substituted by one or more substituents, in particular selected from the substituents chlorine, methoxy, methyl, fluorine and cyano.

These polymer resins are then used to prepare the functionalized SeEA peptide.

By way of solid support ☐, a soluble or insoluble polymer is used, the insoluble polymer preferably being in the form of particles (beads). It is possible for example to use a resin based on polystyrene (preferably) or also based on polyacrylamide, polyethylene glycol, cellulose, polyethylene, polyester, latex, polyamide, polydimethylacrylamide, polyethylene glycol-polystyrene copolymer, polyethylene glycol-polyacrylamide copolymer or also a resin derived therefrom.

In order to prepare the functionalized polymer resin (V) or (V'), a solid support ☐ bearing a suitable functionalization, ☐-Z is used, in which Z is a linker group. Preferably, the solid support has chloro-triphenylmethyl (or chlorotrityl) groups, where the triphenylmethyl is optionally substituted by one or more substituents, in particular selected from the substituents chlorine, methoxy, methyl, fluorine and cyano.

By way of examples of a functionalized solid support ☐-Z, there may be mentioned the polystyrene resins with trityl chloride, 2-chlorotrityl chloride, 4-methyltrityl chloride or 4-methoxytrityl chloride linker groups. Such solid supports are commercially available, for example from Glycopep.

According to another embodiment, the functionalized solid support ☐-Z has linker groups which are groups of the trityl-alcohol type, i.e. OH-Trt-CO—NH— groups, where the triphenylmethyl (Trt) is optionally substituted by one or more substituents, in particular selected from the substituents chlorine, methoxy, methyl, fluorine and cyano. Solid supports with such linker groups have been described for example in Quibell, JACS 1995, 117, 11656-11668, and are commercially available, for example in the ChemMatrix® range of solid polyethylene glycol supports.

The use of solid supports of this type requires a preliminary step of activation of the solid support:
either with a brominated agent (in particular acetyl bromide) in order to modify the linker groups in the Br-Trt-CO—NH— form;
or with a chlorinated agent (in particular oxalyl chloride) in order to modify the linker groups in the Cl-Trt-CO—NH— form;
or with an acid such as trifluoroacetic acid, in order to modify the linker groups in the $H_2O^+$-Trt-CO—NH— form;
or with $BF_3.Et_2O$, in order to modify the linker groups in the $BF_3$:HO-Trt-CO—NH— form. according to Singh, S. et al., *J. Org. Chem.* 2004, 69, 4551-4554.

An activation step of this type is described for example in Harre et al., Reactive & functional polymers 1999, 41, 111-114.

The preparation of the functionalized polymer resin is carried out by coupling the amine compound of formula:

$$NH(CH_2—CH_2—Se—H)_2 \quad \text{(III)}$$

with the above functionalized solid support, ☐-Z. The amine compound (III) can itself be obtained by deprotection of the above amine compound of formula (IIIa), in which $G_1$ is a selenium protective group.

The coupling is carried out in an acid medium in order to limit the risks of unmasking the secondary amine, which would lead to secondary reactions.

The excess trityl chloride groups are preferably neutralized, for example with methanol. It is then important to add a base in order to neutralize the HCl formed.

It can be provided that the preparation of the functionalized polymer resin forms an integral part of the solid-phase production process of the polypeptides of formula (I) and (I').

Alternatively, the functionalized polymer resin can be prepared in advance and separately, in order to be ready for use within the context of the solid phase production process of the peptides of formula (I) and (I').

The use of solid supports of this type can make it possible to use resin backbones of the polyethylene glycol or polyethylene glycol-polystyrene type, more suitable for the preparation of long polypeptides than resins of the polystyrene type.

Preferably, the resin particles have a Dv50 comprised between 1 and 1000 μm. The Dv50 is defined as being the 50th centile of the particle size distribution, i.e. 50% of the particles have a size smaller than the Dv50 and 50% have a size greater than the Dv50. Generally, the Dv50 is characteristic of the granulometric profile (volumetric distribution) of the particles, and it can be determined by laser granulometry (in the case of a size smaller than 200 μm), or by sieving (in the case of a size greater than 200 μm).

Another subject of the invention relates to a peptide grafted onto a functionalized polymer resin with the structure (VII) or (VII'):

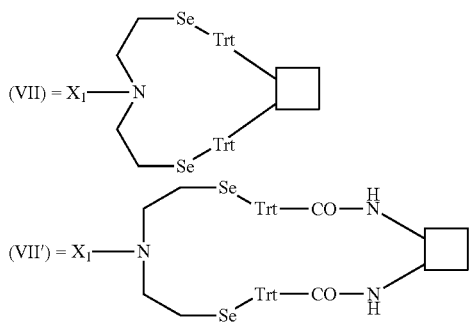

in which,
□ represents a solid support,
Trt represents a triphenylmethyl group optionally substituted by one or more substituents, in particular selected from the substituents chlorine, methoxy, methyl, fluorine and cyano,
$X_1$ represents a peptide fragment functionalized on its C-terminal end.

Solid-Phase Process for Obtaining the Peptides of Formulae (I) and (I')

Another subject of the invention relates to a solid phase production process of the previously described peptides (I) and (I').

This solid-phase process comprises a functionalization phase followed by a peptide synthesis phase.

The first step comprises the provision of a functionalized polymer resin with the structure:

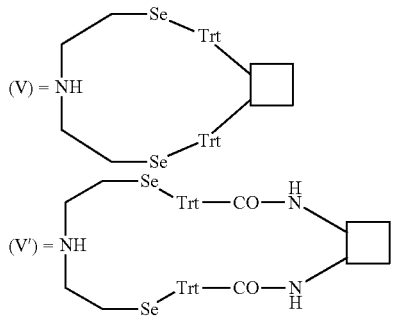

Or
in which
□ represents a solid support,
Trt represents a triphenylmethyl group optionally substituted by one or more substituents, in particular selected from the substituents chlorine, methoxy, methyl, fluorine and cyano.

The second step of the process comprises the grafting of an amino acid $G_3$-AA onto the functionalized polymer resin (V) or (V') obtained in the first step in order to produce the compound of structure (VI):

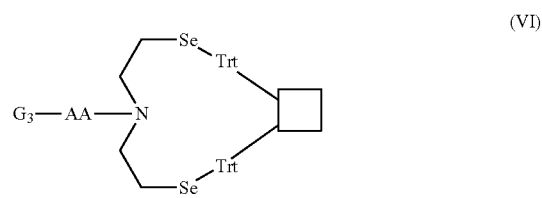

Or of structure (VI'):

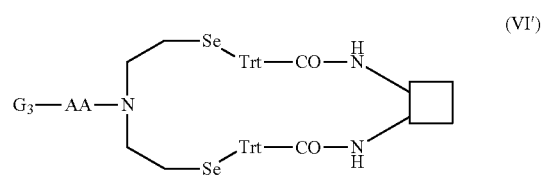

in which,
□ and Trt have the same meaning as in compound (V) or (V'),
AA represents an amino acid residue optionally comprising one or more protective groups;
$G_3$ represents a hydrogen atom or a protective group of the N-terminal amine function of AA.

Preferably the amino acid AA is protected at its N-terminal end by a protective group $G_3$ which is labile in the presence of a base, preferably selected from the 2-(4-nitrophenylsulphonyl)ethoxycarbonyl (NSC) or Fmoc groups.

Preferably, the amino acid AA comprises protective groups on all or some (preferably all) of the functions present on its side chain, and in particular the carboxylic acid (aspartic and glutamic acids), amine (for lysine), alcohol (for serine or threonine), phenol (for tyrosine), thiol or selenol (for cysteine or selenocysteine), guanidine (for arginine) and imidazole (for histidine) functions. Such protective groups are known to a person skilled in the art. Reference may be made for example to the reference work *Protective groups in organic synthesis*, 2nd edition, T. Greene and P. Wuts, John Wiley & Sons, Inc.

Preferably, the amino acid is activated in the presence of HATU (2-(1H-7-Azabenzotriazol-1-yl)-1,1,3,3-tetramethyl uronium hexafluorophosphate Methanaminium), of PyBOP or of BOP or more particularly preferably in the presence of PyBROP, or also in the form of a halide, in particular a fluoride (i.e. a fluorine atom is linked to the acyl group of the amino acid residue).

The amino acid reacts with the secondary amine function present on the functionalized solid support in order to form an amide bond. After coupling of the amino acid, the latter may optionally be deprotected.

Thus, in this embodiment, the functionalization step consists of creating a primer solid support from a previously functionalized solid support.

The third step comprises peptide synthesis starting from the amino acid AA grafted onto the polymer resin in order to produce compound (VII) or (VII'):

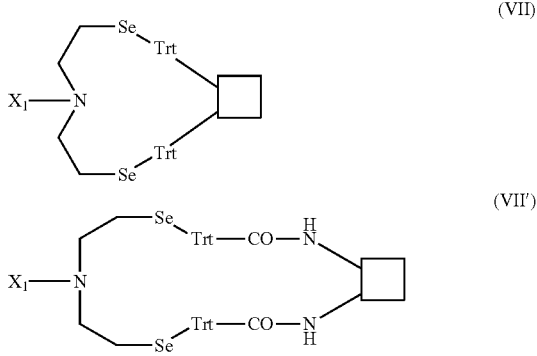

The peptide synthesis step is carried out analogously to what has already been described previously, relating to liquid-phase peptide synthesis, the initial primer being provided by the amino acid AA grafted onto the solid support.

Finally, once the peptide synthesis is completed, a reaction of separation (or cleavage) of the polypeptide from its support is provided, by cleavage of the bond between Trt and Se in order to produce compound (I) or (I'). Preferably, the cleavage is carried out with a trifluoroacetic acid solution comprising the carbocation traps known to a person skilled in the art such as water, triisopropylsilane, thiophenol, thioanisole, anisole, dimethyl sulphide, etc.

Suitable deprotections of the side chains of the amino acids may also optionally be provided in order to obtain a functionalized peptide of formula (I) or (I').

As for the liquid-phase process, it is advantageous to provide at this stage a compound purification step, for example by liquid chromatography.

Native Ligation Process

Another subject of the invention relates to a process for producing a polypeptide of formula (VIII):

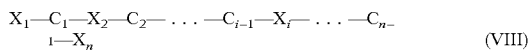

in which,
$X_1, X_2, \ldots, X_i, \ldots, X_n$ are peptide fragments,
$C_1, C_2, \ldots, C_{i-1}, C_{n-1}$ are amino acid residues bearing a thiol, or selenol function
n is an integer greater than or equal to 2,
i is any integer in the range from 1 to n,
this process comprising one or more steps of reaction between a compound of formula $(IX_i)$:

in which:
$X'_1$ represents $X_1$
and $X'_i$ represents $C_{i-1}—X_i$ for i>1
and a compound of formula $(X_{i+1})$:

in order to form a compound of formula $(X_i)$:

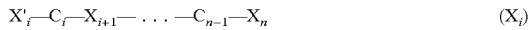

The residue $C_i$ is an amino acid residue comprising a thiol or selenol function. This thiol or selenol function can be in particular a beta-amino thiol function or beta-amino selenol function (in which case the $C_i$ residue preferably represents the cysteine residue or the selenocysteine residue), a gamma-amino thiol or gamma-amino selenol function (in which case the $C_i$ residue preferably represents the homocysteine or homoselenocysteine residue).

The invention makes it possible to produce polypeptides by successively carrying out several ligation reactions. This can prove appropriate in order to obtain large-sized polypeptides, for example polypeptides comprising more than approximately 100 amino acid residues. In fact, in such cases the production of polypeptides of formulae $(IX_i)$ and $(X_i)$ by direct synthesis can have a low yield, and it is therefore advantageous to use two or more than two successive ligations, in order to have to directly synthesize only polypeptides comprising for example less than approximately 50 amino acid residues.

By way of example, the use of two successive ligations makes it possible to obtain a polypeptide comprising approximately 150 amino acid residues without having to directly synthesize polypeptide comprising more than approximately 50 amino acid residues; the use of three successive ligations makes it possible to obtain a polypeptide comprising approximately 200 amino acid residues without having to directly synthesize polypeptide comprising more than approximately 50 amino acid residues.

The polypeptide of formula (VIII) can be obtained by using several ligation methods. Other ligation methods are for example methods involving thioesters or involving particular sulphur-containing compounds as described in WO 2011/051906.

The process for producing the polypeptide of formula (VIII) according to the invention comprises at least one reaction step between a compound of formula $(IX_i)$ and a compound of formula $(X_i)$.

Thus, the process according to the invention makes it possible to obtain a polypeptide of formula (VIII); each $X_i$ for i an integer between 1 and n, being a peptide fragment; and each $C_i$, for i an integer between 1 and n, being an amino acid residue comprising a thiol or selenol function, and in particular a cysteine or selenocysteine residue according to a particular embodiment, using n−1 successive ligations.

According to an embodiment of the invention, compound $(IX_i)$ can be obtained from compound $(IX'_i)$:

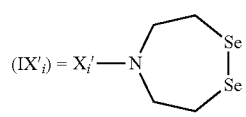

in the presence of at least one compound that reduces diselenium and/or triselenium bonds. In fact, the polypeptide of formula $(IX'_i)$ is then reduced in situ and provides the polypeptide of formula $(IX_i)$ for the ligation reaction.

According to an embodiment, the reducing compound is selected from tris(2-carboxyethyl)phosphine (TCEP), 4-mercaptophenylacetic acid (MPAA), benzylmercaptan, thiophenol, DTT, sodium 2-mercaptoethylsulphonate (MESNa), selenophenol.

Analogously to what was described previously for compounds (I) and (I'), according to an embodiment, the compounds $(IX_i)$ and $(IX'_i)$ can be formed by exchange, starting from an SEA segment of structure $X'_i—N(CH_2CH_2—S-G_5)_2$ or from a thioester of structure $X'_i—S—R_1$ using the selenium-containing compounds of structure (III') or (III''), optionally in the presence of compounds that reduce disulphide and/or diselenium bonds, $G_5$ representing H, a protective group of the thiol function or a disulphide bond and $R_1$ representing H or a protective group of sulphur.

In the case where i is equal to 1, compounds $(IX_i)$ and $(IX'_i)$ correspond to compounds (I) and (I') respectively.

Generally, the ligation reaction starting from the polypeptide of formula $(IX'_i)$ as reagent can be more practical to implement than the ligation reaction directly with the polypeptide of formula $(IX_i)$. In fact, the polypeptide of formula $(IX_i)$ has a natural tendency to oxidize to the polypeptide of formula $(IX'_i)$, in particular under the action of the oxygen in the air. For example, it is possible that the open-form polypeptide $(IX_i)$ oxidizes over time when it is stored in the lyophilized form. In other words, a preparation of the polypeptide of formula $(IX_i)$ generally necessarily partly contains the polypeptide of formula $(IX'_i)$. The presence of these two forms can complicate characterization and purification. This is why it may be simpler to implement the ligation reaction by placing the polypeptide of formula $(IX'_i)$ in contact with the polypeptide of formula $(X_i)$, the polypeptide with the cyclic termination of formula $(IX'_i)$ being reduced in situ to the open polypeptide of formula $(IX_i)$.

For the same reasons, even when the ligation reaction is carried out directly by placing the polypeptide of formula $(IX_i)$ in contact with the polypeptide of formula $(X_i)$, it is preferable to use one or more of the above-mentioned compounds that reduce diselenium bonds during the reaction.

The ligation reaction preferably takes place in liquid phase, and in particular in an aqueous medium, for example in a phosphate buffer. Preferably, this reaction is carried out at a pH comprised between 4 and 8.5, more particularly preferably at a pH comprised between 5 and 7.5 and ideally at a pH close to 5.5.

The ligation reaction is preferably carried out at a temperature comprised between 0 and 50° C., and ideally at a temperature of approximately 37° C. The duration of the reaction is adjusted as a function of the selection of the reagents and other conditions of the reaction. The appropriate duration can also be adjusted according to the results of a liquid chromatography—mass spectrometry analysis during the reaction. The appropriate duration is typically from a few hours to a few days.

Each of the polypeptides of formula $(IX_i)$ and $(X_i)$ is preferably present in a concentration comprised between 0.01 and 50 mM, during the reaction. The molar concentration ratio between the polypeptides of formula $(IX_i)$ and $(X_i)$ during the reaction is preferably comprised between 2:3 and 3:2.

The ligation reaction described above can be followed by a step of purification of the polypeptide of formula $(X_i)$ obtained, for example by liquid chromatography or by any other usual technique.

The ligation kinetics according to the present invention are significantly superior to the ligation kinetics obtained with sulphur-containing compounds described in the document WO 2011/051906 or with thioesters such as those taught by Kent and Dawson.

Due to the rapidity of the SeEA ligation, it can be carried out in the presence of other groups capable of participating in a native ligation reaction, such as the SEA or thioester segments.

The combination of the SeEA and SEA ligations constitute a very efficient tool for the total synthesis of proteins. For the production of a protein which must be synthesized by ligation of several fragments it is possible for example to implement SEA ligation for the easy junctions, and SeEA ligation for the difficult junctions. In fact, SeEA ligation makes it possible to easily form hindered junctions, for example in 4 hours for the Val-Cys junction, whereas this type of junction requires ligation times of 96 hours in the case of SEA ligation or 8 hours in the case of NCL ligation.

Another useful way of using SeEA and SEA ligations is one-pot sequential SeEA-SEA ligation. The latter can be implemented in order to link three fragments without isolation and intermediate purification (known as "one-pot reaction") when the junctions have an analogous steric hindrance. An embodiment example of this variant is explained below.

According to an embodiment of the invention, the ligation process of the invention allows the production from three peptide fragments, of a polypeptide represented by formula (XII):

said polypeptide being obtained by a process comprising the following steps:

a) reaction between a compound of formula (XIII) or (XIII'):

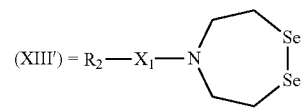

and a compound of formula (XIV) or (XIV'):

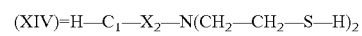

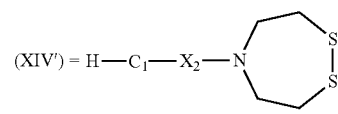

in order to form the compound of formula (XV) or (XV'):

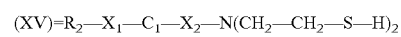

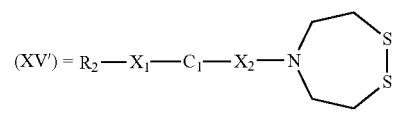

b) reaction between a compound of formula (XV) or (XV') and a polypeptide of formula (XVI):

$$H\text{—}C_2\text{—}X_3 \qquad (XVI)$$

in order to form the compound of formula (XII), in which, $R_2$ represents a protective group of the N-terminal function of $X_1$, $X_1$, $X_2$, $X_3$ represent, independently of each other, peptide fragments, $C_1$ and $C_2$ represent, independently of each other, amino acid residues bearing a thiol or selenol function.

In a manner analogous to what is described previously for obtaining compounds (I) and (I'), the above compounds (XIII) and (XIII') can be formed in situ, by exchange starting from reagents of the (IIIa), (III') or (III") type in the presence of SEA compounds of structure $R_2$—$X_1$-SEA or thioester of structure $R_2$—$X_1$—S—$R_1$, in which $R_1$ represents H or an optionally substituted alkyl or aryl, thus making it possible to accelerate the second ligation step.

This one-pot three-segment ligation reaction can be implemented in order to link three fragments without isolation and intermediate purification (known as "one-pot reaction") when the junctions have an analogous steric hindrance. As the hindrance of the junctions is analogous, the ligation between compound (XIII) or (XIII') and compound (XIV) or (XIV') is more rapid than the cyclization of compound (XIV) or (XIV') by intramolecular SEA ligation, or the polymerization of the segment (XIV) or (XIV') by intermolecular SEA ligation. The intramolecular or intermolecular SEA ligations are described in WO 2011/051906.

Production of a Cyclic Polypeptide by Native Self-Ligation

The principles used for native ligation described above can also be used to produce cyclic polypeptides, by native self-ligation of a polypeptide (ligation of one end of the polypeptide with the other end of the same polypeptide).

Another subject of the invention relates to a process for producing a cyclic polypeptide of formula (XVII):

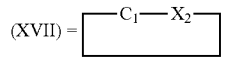

$X_2$ representing a peptide fragment, and $C_1$ representing an amino acid residue comprising a thiol or selenol function, said process comprising at least one reaction step of ligation of a polypeptide of formula (XVIII):

$$H-C_1-X_2-N(CH_2-CH_2-Se-H)_2 \quad (XVIII)$$

with itself.

The polypeptide of formula (XVIII) preferably comprises between 2 and 300 amino acid residues, preferably between 5 and 100 amino acid residues, more particularly preferably between 8 and 50 amino acid residues.

The polypeptide of formula (XVIII) comprises a hydrogen atom and a $C_1$ residue at the N-terminal end, $C_1$ having the meaning indicated above. $X_2$ here represents a peptide fragment of the form $AA_1AA_2 \ldots AA_n$, where n is an integer greater than or equal to 1 and each $AA_i$ represents an amino acid residue.

The polypeptide of formula (XVIII) preferably comprises only amino acid residues selected from the twenty proteinogenic amino acid residues and selenocysteine. However, according to a particular embodiment, the polypeptide of formula (XVIII) comprises one or more non-proteinogenic amino acid residues, other than selenocysteine.

The amino acid residues of the polypeptide of formula (XVIII) can optionally be protected by side chain protective groups.

It is possible to carry out the above ligation reaction by placing the polypeptide of formula (XVIII'):

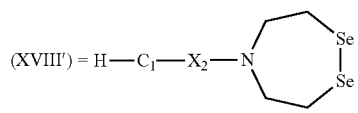

in contact with at least one compound that reduces diselenium bonds, which is preferably as described above. In fact, the polypeptide of formula (XVIII') is then reduced in situ and provides the polypeptide of formula (XVIII) for the ligation reaction.

Generally, even when the ligation reaction is carried out directly from the polypeptide of formula (XVIII), it is preferable to use one or more of the above-mentioned compounds that reduce diselenium bonds during the reaction.

In general, the cyclization of the polypeptide of formula (XVIII) is not impeded by concurrent multimerizations, if the reaction is carried out under sufficiently dilute conditions. It is possible for example to use a concentration of polypeptide of formula (XVIII) comprised between 0.01 and 50 mM, typically of approximately 1 mM (or optionally between 0.01 and 0.1 mM in the case of serious risks of multimerizations).

Moreover, the preferred conditions for implementation of the ligation reaction are the same as those described above for the reaction starting from the polypeptides of formula (IX) and (X).

The ligation reaction described above can be followed by a step of purification of the cyclic polypeptide of formula (XVII) obtained, for example by liquid chromatography or by any other usual technique.

Synthesis Kit

Another subject of the invention relates to a polypeptide synthesis kit comprising one or more peptides of formulae $(IX_i)$ or $(IX'_i)$, or at least one compound of formula (III') or (III''), and optionally one or more coupling, protection, deprotection reagents, or solvents.

EXAMPLES

Example 1

Synthesis of Compounds 1 ($Se_2EA$) and 2 ($Se_3EA$)

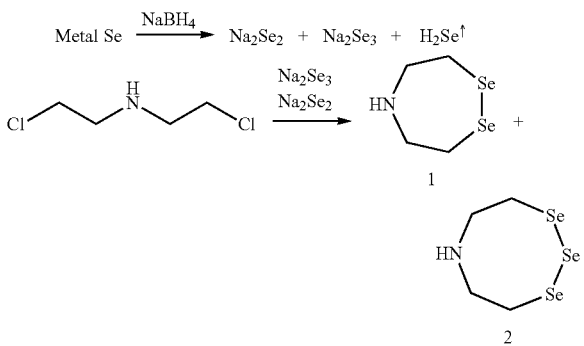

Under nitrogen flushing, absolute ethanol V=19 mL is added dropwise, under stirring, to a mixture of selenium Se (940 mg, 11.9 mmol, 1.5 eq) and sodium borohydride (NaBH$_4$) (300 mg, 7.9 mmol) cooled down in an ice bath. After a vigorous reaction, the reaction medium is taken to reflux for 1 hour 30 minutes. The sodium diselenide Na$_2$Se$_2$ formed in solution is reddish brown in colour.

At ambient temperature, bis(2-chloroethyl)amine hydrochloride (847 mg, 4.7 mmol, 0.5 eq) in solution in an NaOHaq (0.5 M)/EtOH (1/1) mixture V=3 mL is added dropwise to the above solution of Na$_2$Se$_2$ and Na$_2$Se$_3$ over 10 minutes. The reaction medium is stirred for 45 minutes at ambient temperature.

The reaction medium is then diluted V=10 mL with a solution of NaOHaq (0.5M) then extracted with CH$_2$Cl$_2$ (3×30 mL). The organic phases are then combined, dried with Na$_2$SO$_4$, then concentrated to ⅓ of the total volume.

The organic concentrate obtained is then extracted with an aqueous solution of trifluoroacetic acid (TFA) (10%) then purified directly by RP-HPLC: Xbridge C18 Column (d=1.9 cm, L=20 cm, 130 Å, 5 µm), UV detection (λ=215 nm), buffer A: H$_2$O/TFA (1:0.05% v/v), buffer B: CH$_3$CN/H$_2$O/TFA (4:1:0.05% v/v/v), isocratic: buffer A (3 min), then gradient: buffer B (0 to 50% over 9 min, 25 mL/min)

After lyophilization, compounds 1 (Se$_2$EA) 230 mg (Yield Y=21%) and compounds 2 (Se$_3$EA) 240 mg (Yield Y=16%) are obtained in the form of a yellow powder.

LC-MS Analysis, RP-HPLC Chromatogram of Compounds 1 (Se$_2$EA) and 2 (Se$_3$EA) Respectively LC-MS: Buffer A: H$_2$O/TFA (1/0.1% v/v), Buffer B: CH$_3$CN/H$_2$O/TFA (4/1:0.1% v/v/v).

RP-HPLC on an XBridge BEH C18 column (300 Å, 3.5 µm, 4.6×150 mm) using a linear gradient 0-100% B over 30 minutes, flow rate 1 mL/min, UV detection (λ=215 nm).

MS: Electrospray ionization positive mode, voltage cone 30V, quadripolar analyser.

The chromatogram and the mass spectrum of compound 1 are shown in FIGS. 1a and 1b respectively.

Figure 2A:
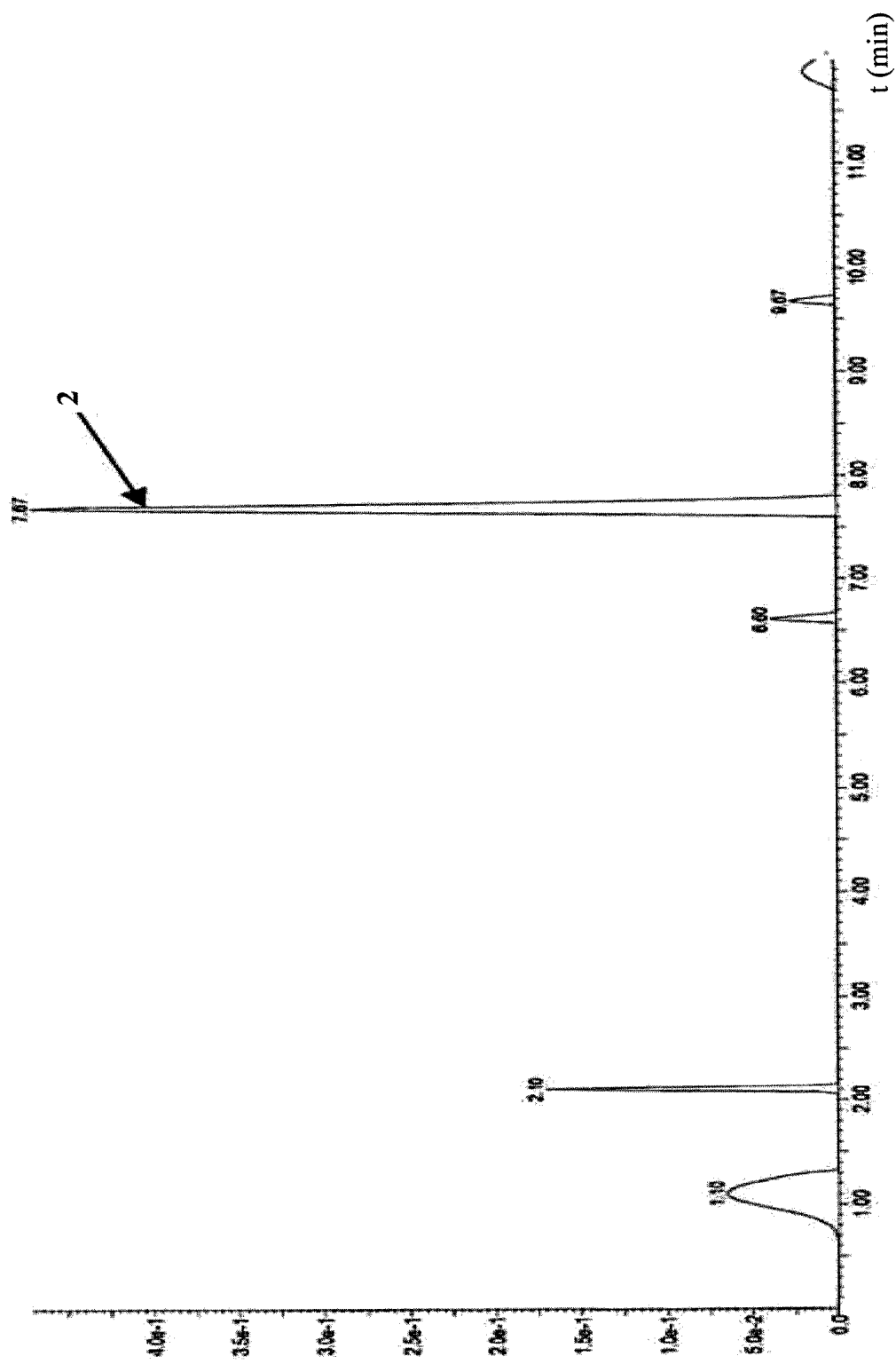
FIGS. 2a and 2b represent respectively the HPLC chromatogram and the mass spectrum of a selenium-containing compound according to the invention.
Figure 2B:
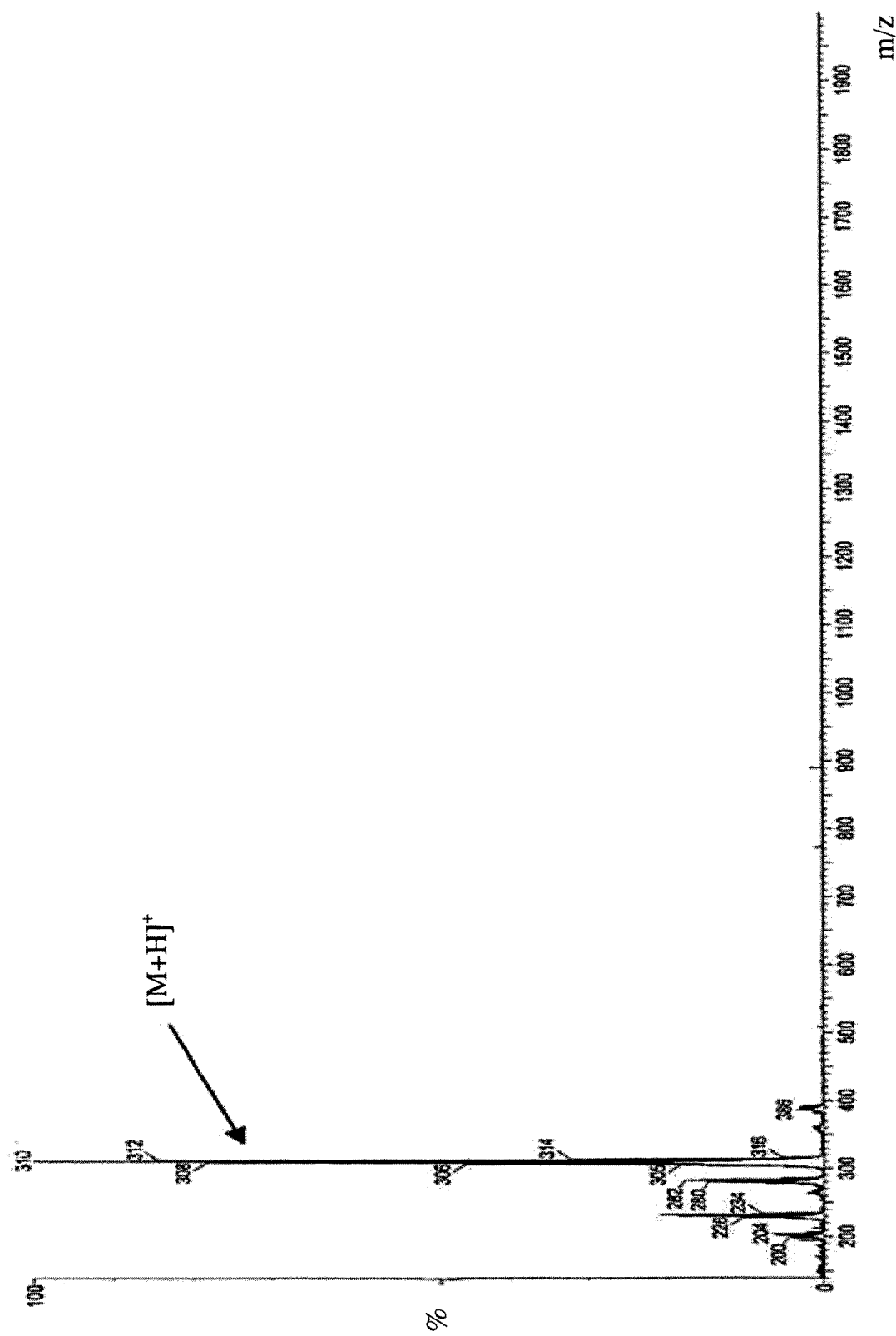

The chromatogram and the mass spectrum of compound 2 are shown in FIGS. 2a and 2b respectively.

Example 2

Synthesis and Isolation of the SeEA Segments According to the Invention by Exchange, Starting from SEA Segments Synthesis of Peptide 8: H-ILKEPVHGA-SEA The method for the synthesis of this peptide is described in the document Ollivier, N.; Dheur, J.; Mhidia, R.; Blanpain, A.; Melnyk, O. *Organic letters* 2010, 12, 5238-41.

Synthesis of Peptide 9: H-ILKEPVHGA-SeEA

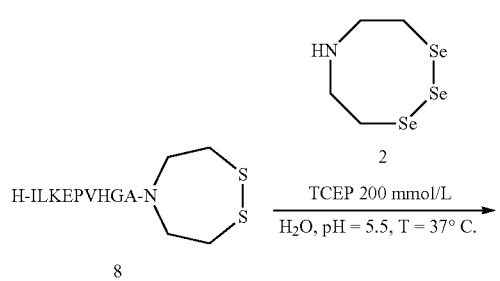

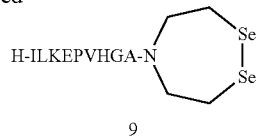

The reaction is carried out in a glove box (the dioxygen concentration is less than 50 ppm) under a nitrogen atmosphere. A 200 mmol/L solution of TCEP is prepared in a 0.1M phosphate buffer at pH=7.2. The pH of the TCEP/MPAA solution obtained is adjusted to pH=5.5.

Peptide 8 (3.8 mg, 3 µmol) and Se$_3$EA linker 2 (8.4 mg, 28 µmol, 10 eq) are dissolved in the above solution of TCEP V=297 µL. The reaction medium is stirred for 24 hours at 37° C.

At the end of the reaction, the reaction medium is diluted V=2 mL with a solution of TFA (0.1%) then purified directly by reversed-phase high-performance liquid chromatography (RP-HPLC) (C18 Nucleosil column (d=1 cm, L=20 cm, 120 Å, 5 µm), UV detection (λ=215 nm), buffer A: H$_2$O/TFA (1:0.05% v/v), buffer B: CH$_3$CN/H$_2$O/TFA (4:1:0.05% v/v/v), gradient: buffer B (0 to 20% over 5 min then 20 to 42% over 60 min, 6 mL/min)) 1.96 mg of peptide 9 is obtained (yield 62%).

LC-MS Analysis, RP-HPLC Chromatogram of Peptide 9

LC-MS: Buffer A: H$_2$O/TFA (1/0.1% v/v), Buffer B: CH$_3$CN/H$_2$O/TFA (4/1:0.1% v/v/v).

RP-HPLC on an XBridge BEH C18 column (300 Å, 3.5 µm, 4.6×150 mm) using a linear gradient 0-100% B over 30 minutes, flow rate 1 mL/min, UV detection (λ=215 nm).

MS: Electrospray ionization positive mode, voltage cone 30V, quadripolar analyser.

Figure 3A:
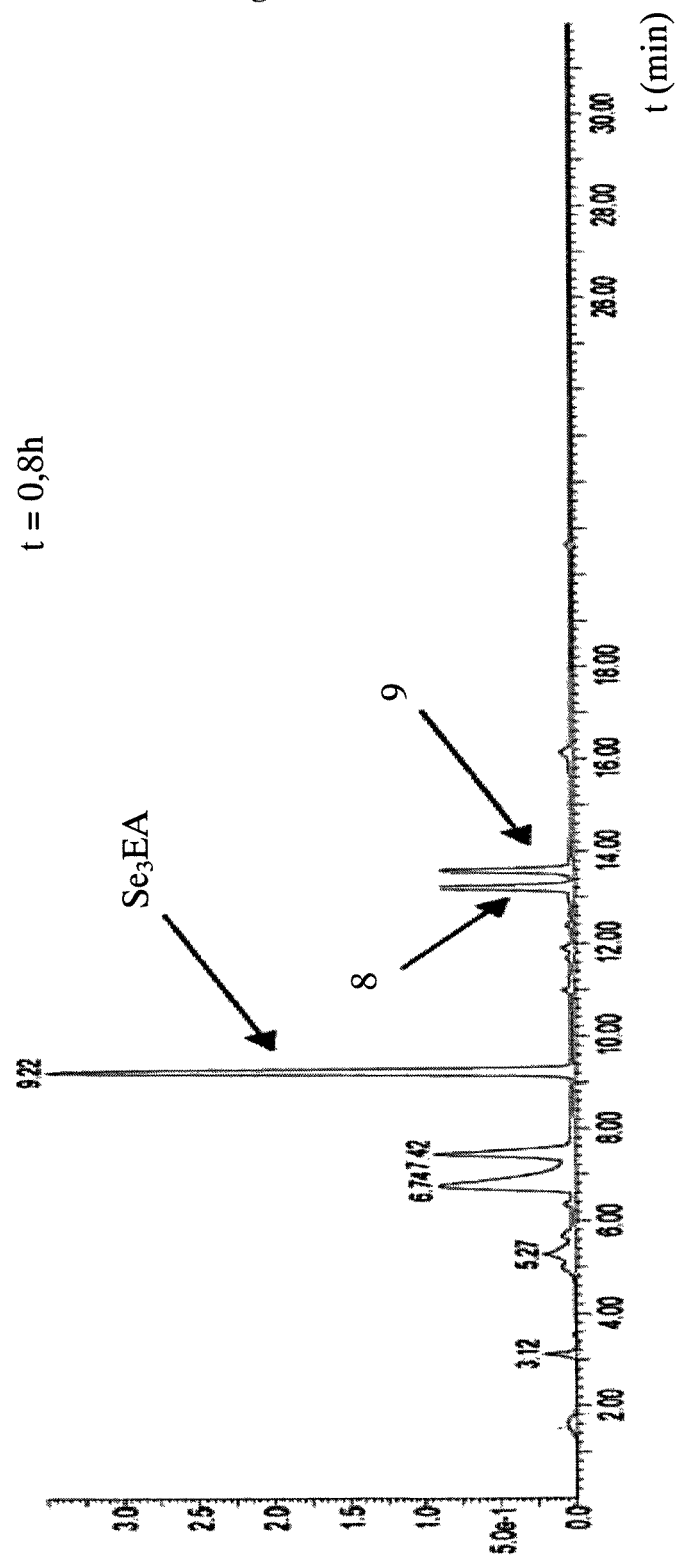
FIGS. 3a and 3b represent HPLC chromatograms for monitoring the synthesis of a functionalized peptide according to the invention.

FIG. 3a corresponds to the chromatogram of the solution after a reaction time t of 0.8 hour. For t=0.8 hour, the exchange reaction is not completed, in fact, the peak corresponding to peptide 8 is still present in a significant quantity.

Figure 3B:
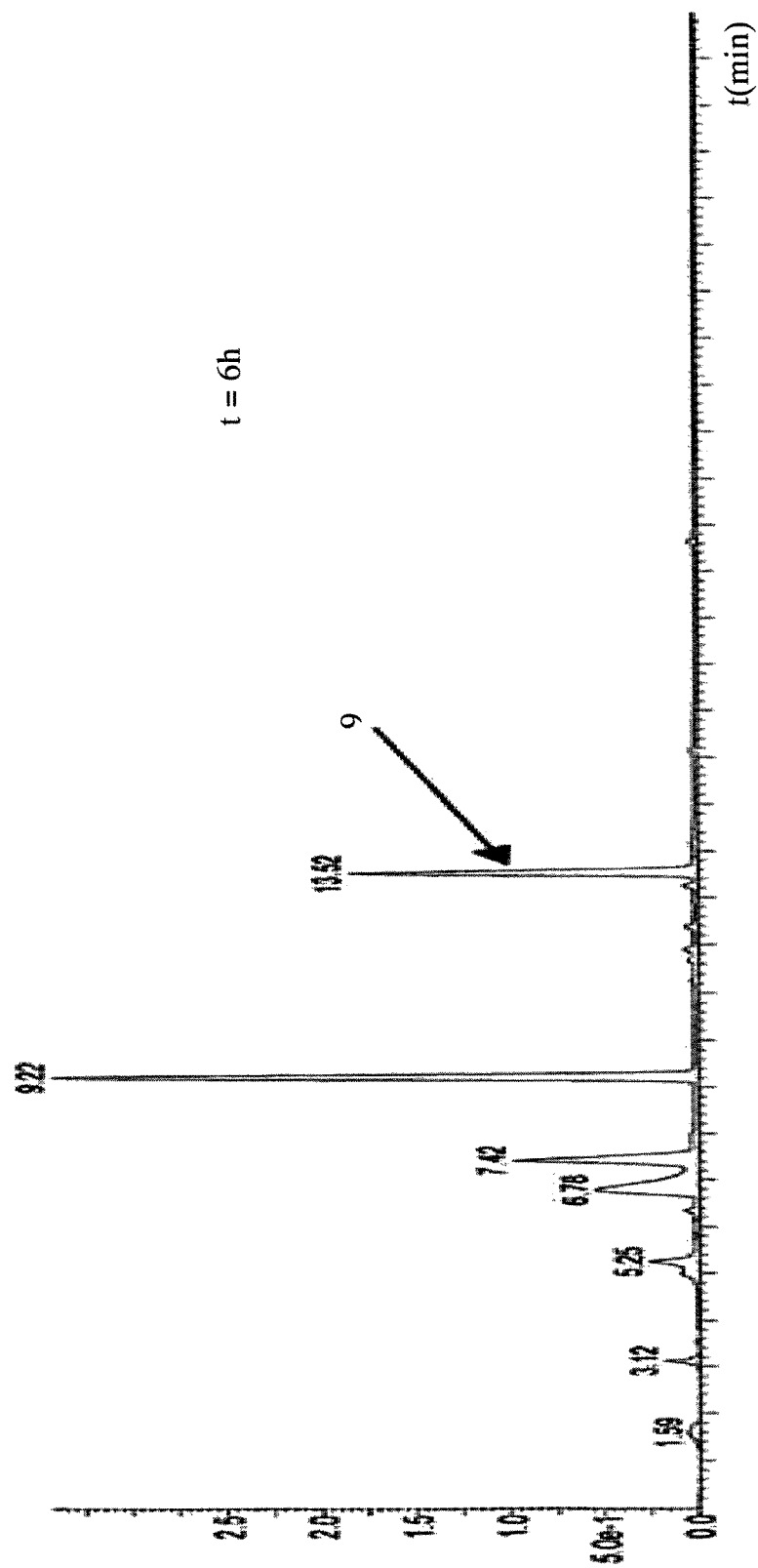
Figure 3C:
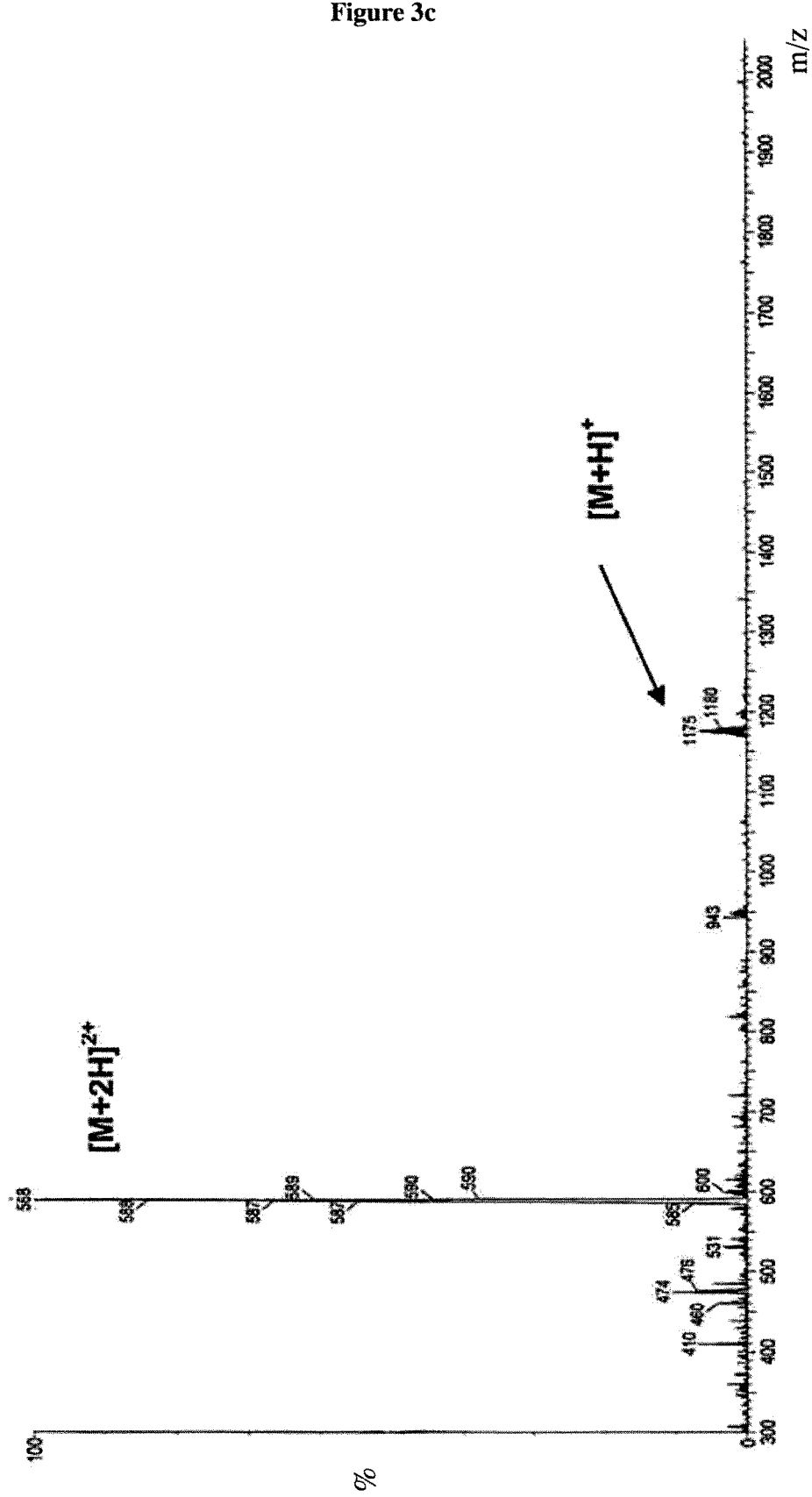
FIG. 3c represents the mass spectrum of a functionalized peptide according to the invention.

FIG. 3b corresponds to the chromatogram of the solution after a reaction time t of 6 hours and FIG. 3c is the corresponding mass spectrum. This chromatogram shows that the exchange reaction is completed.

Figure 4A:
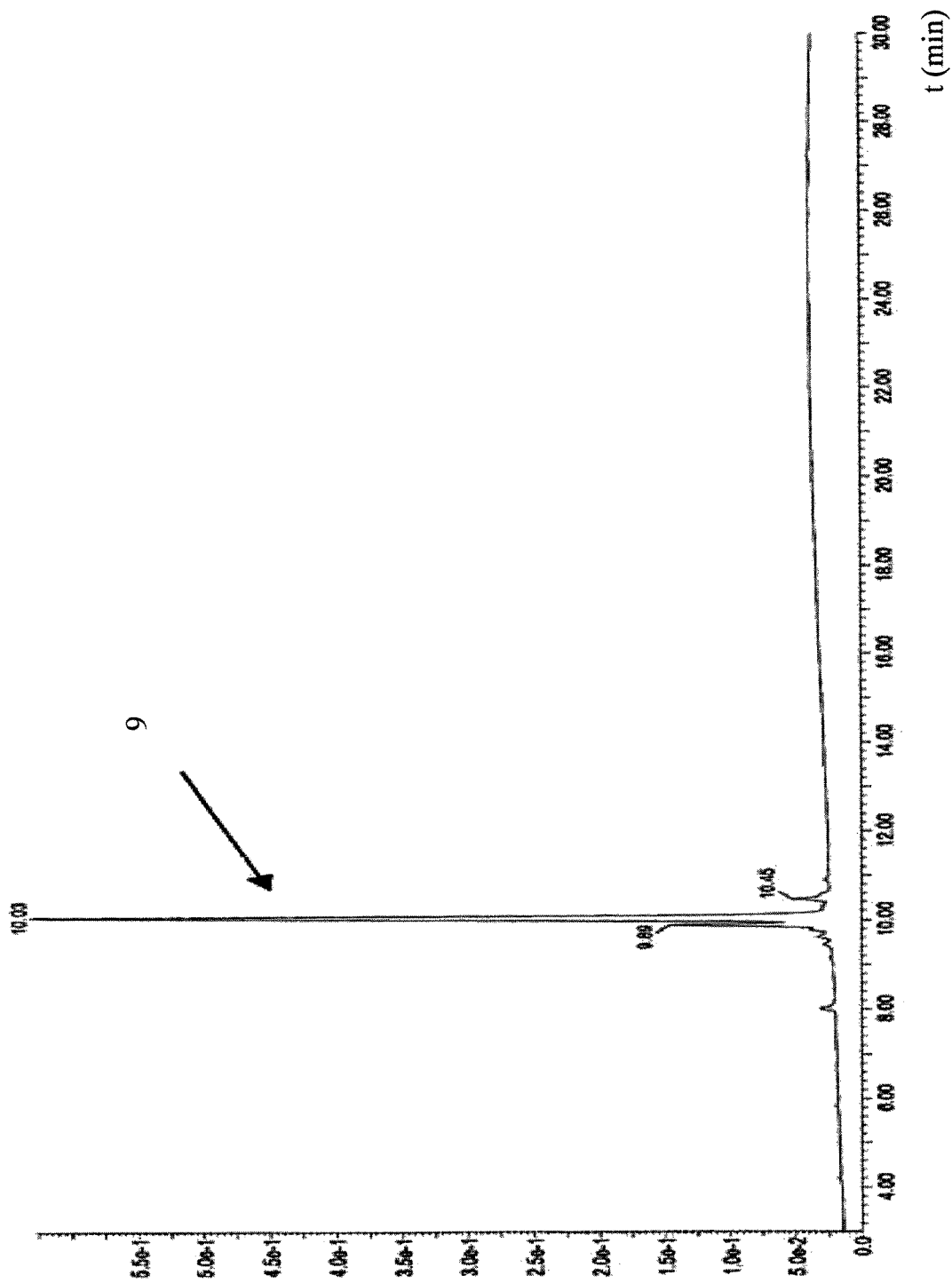
FIGS. 4a and 4b represent respectively the HPLC chromatogram and the mass spectrum of a functionalized peptide according to the invention.
Figure 4B:
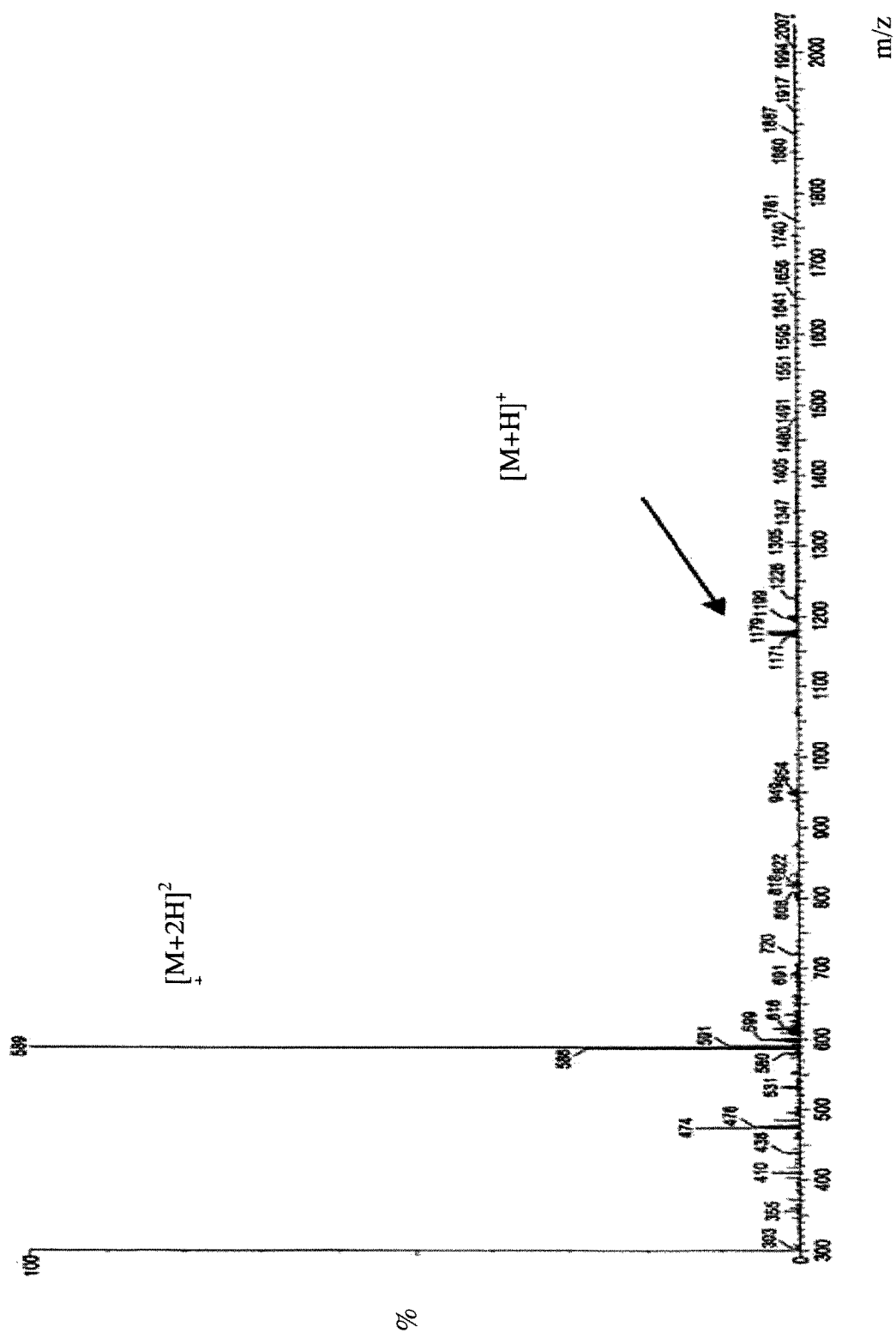

FIGS. 4a and 4b correspond to the chromatogram and the mass spectrum of peptide 9 after purification.

Example 2a

Synthesis and Isolation of Large SeEA Segments According to the Invention by Exchange, Starting from SEA Segments Synthesis of Peptide 15: H-IRNCIIGKGRSYKGTVSITKS-GIK-SEA The method for the synthesis of this peptide is described in the document Ollivier, N.; Dheur, J.; Mhidia, R.; Blanpain, A.; Melnyk, O. *Organic letters* 2010, 12, 5238-41.

Synthesis of Peptide 16: H-IRNCIIGKGRSYKGTVSITKSGIK-SeEA

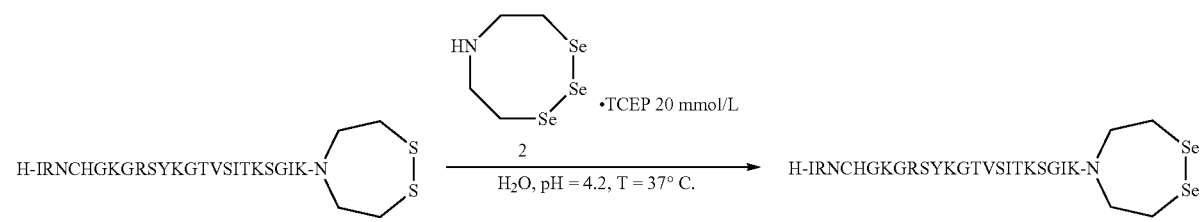

The reaction is carried out under a nitrogen atmosphere. A 20 mmol/L solution of TCEP is prepared in a 0.1M acetate buffer at pH=5.5. The pH of the solution TCEP obtained is adjusted to pH=4.2.

Peptide 15 (4 mg, 1.4 μmol) and Se₃EA linker 2 (4.4 mg, 14.3 μmol, 10 eq) are dissolved in the above solution of TCEP V=719 μl. The reaction medium is stirred for 24 hours at 37° C.

At the end of the reaction, the reaction medium is diluted V=3 mL with a solution of TFA (0.1%) then purified directly by reversed-phase high-performance liquid chromatography (RP-HPLC) (C18 Nucleosil column (d=1 cm, L=20 cm, 120 Å, 5 μm), UV detection (λ=215 nm), buffer A: H₂O/TFA (1:0.05% v/v), buffer B: CH₃CN/H₂O/TFA (4:1:0.05% v/v/v), gradient: buffer B (0 to 20% over 5 min then 20 to 42% over 60 min, 6 mL/min)) 1.8 mg of peptide 16 is obtained (Yield 38%).

LC-MS Analysis, RP-HPLC Chromatogram of Peptide 16
LC-MS: Buffer A: H₂O/TFA (1/0.1% v/v), Buffer B: CH₃CN/H₂O/TFA (4/1:0.1% v/v/v).

RP-HPLC on an XBridge BEH C18 column (300 Å, 3.5 μm, 4.6×150 mm) using a linear gradient 0-100% B over 30 min, flow rate 1 mL/min, UV detection (λ=215 nm).

MS: Electrospray ionization positive mode, voltage cone 30V, quadripolar analyser.

Figure 13:
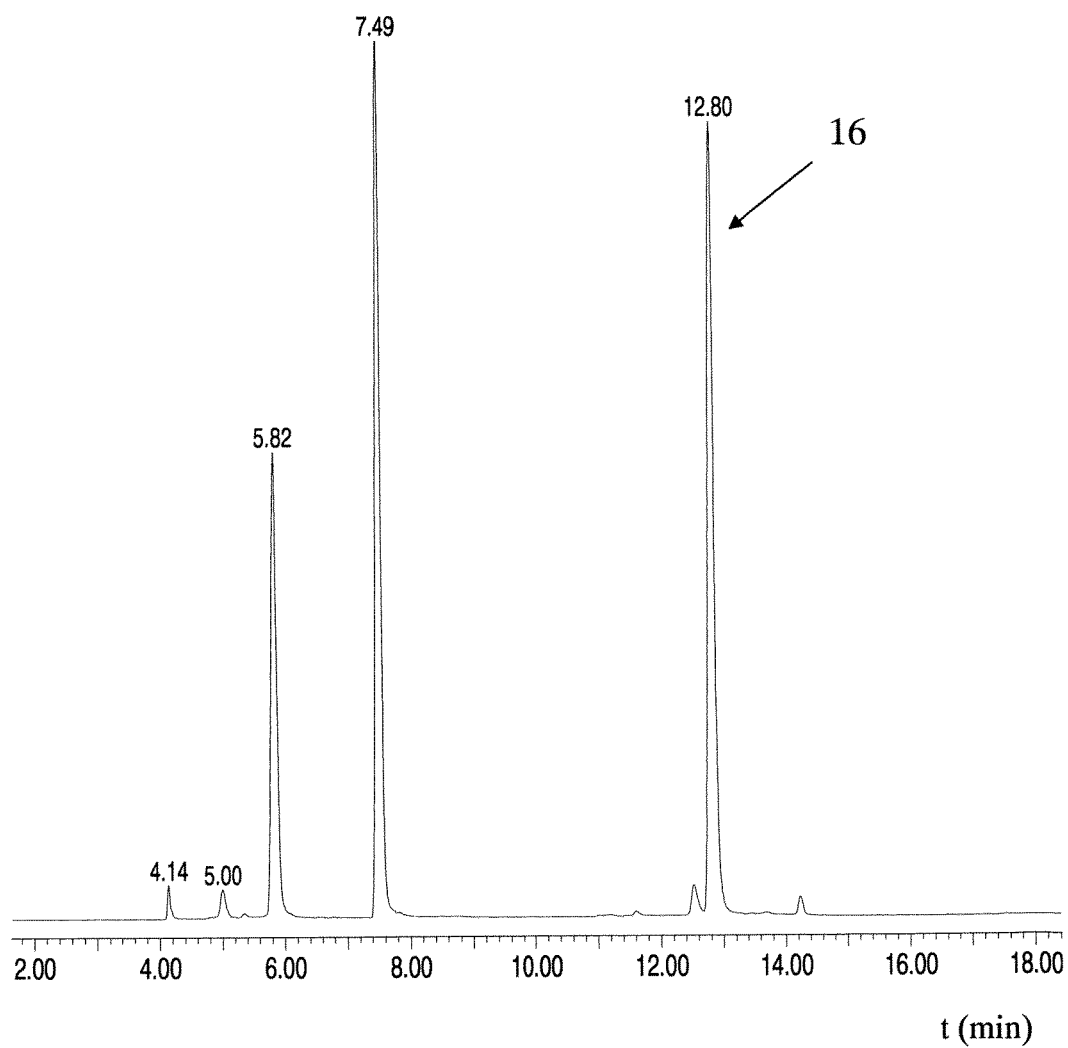
FIG. 13 represents an HPLC chromatogram of a solution originating from the synthesis of a functionalized peptide according to the invention.

FIG. 13 corresponds to the chromatogram of the solution after a reaction time t of 24 hours. The peak corresponding to peptide 16 is clearly present and indicates that the exchange reaction is completed.

Figure 14A:
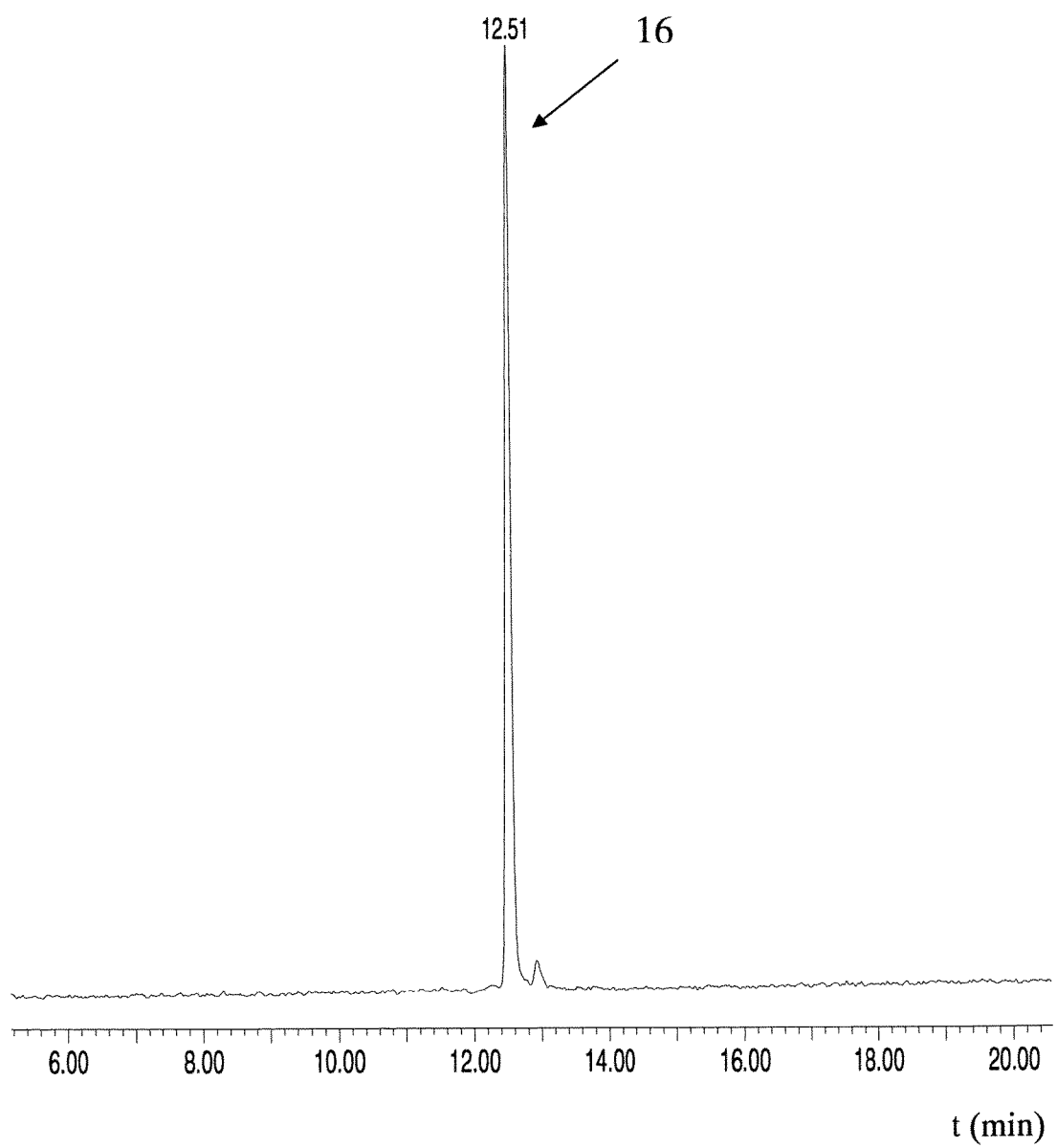
FIGS. 14a and 14b represent respectively the HPLC chromatogram and the mass spectrum of a functionalized peptide according to the invention.
Figure 14B:
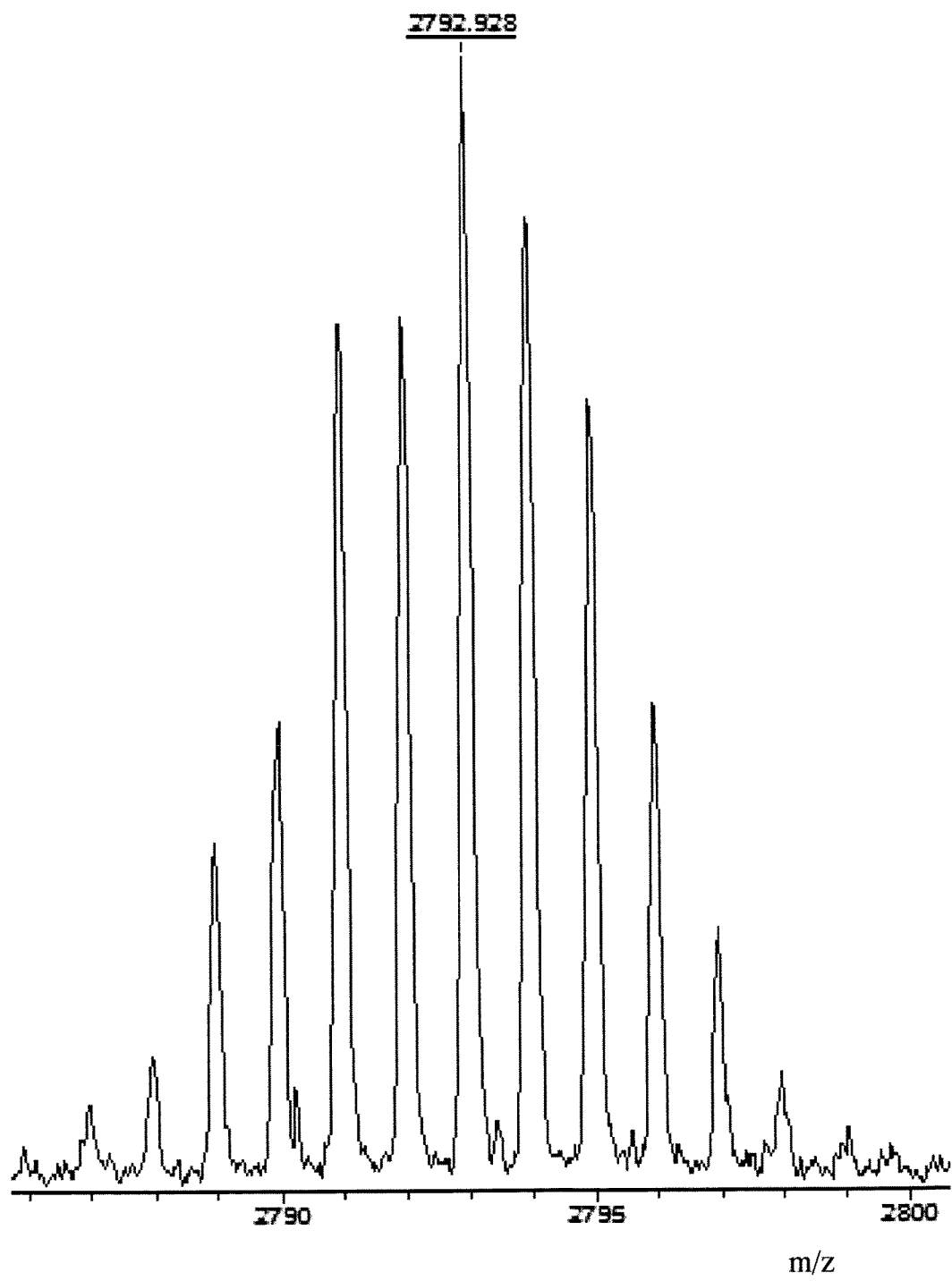

FIGS. 14a and 14b correspond respectively to the chromatogram and to the mass spectrum of peptide 16 after purification.

Example 3

Native Ligation with Selenium-Based Compounds According to the Invention or Sulphur-based Compounds According to the Prior Art Synthesis of Peptide 3, SEQ ID NO: 1 Ac-GFGQGFGG-OH
The method for the synthesis of this peptide is described in the document Ollivier, N.; Dheur, J.; Mhidia, R.; Blanpain, A.; Melnyk, O. *Organic letters* 2010, 12, 5238-41.

Synthesis of Peptide 4: Ac-GFGQGFGG-SeEA

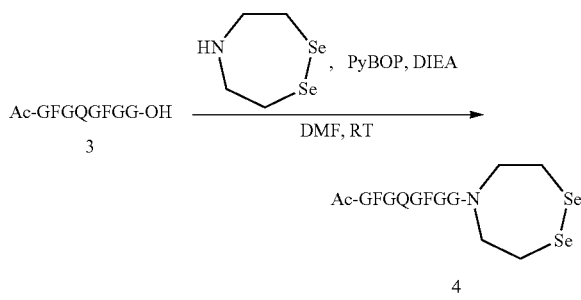

Peptide 3 (50 mg, 0.07 mmol) and molecule 1 (30 mg, 0.13 mmol, 2 eq) are dissolved in V=3.5 mL of DMF (N,N-dimethylformamide) followed by the addition of benzotriazol-1-yloxy-tripyrrolidinophosphoniumhexafluorophosphate (PyBOP) (68 mg, 0.14 mmol, 2 eq). N,N-diisopropylethylamine (DIEA) is then added (45 μL, 0.28 mmol, 4 eq). The reaction medium is stirred for 1.5 hours at ambient temperature then precipitated from a cold mixture of diethyl ether/heptane (75 mL, 1:1 v/v), centrifuged, then dissolved in a minimum amount of water and lyophilized.

Raw peptide 4 is purified directly by reversed-phase high-performance liquid chromatography (RP-HPLC) (C18 Nucleosil column (d=1 cm, L=20 cm, 120 Å, 5 μm), UV detection (λ=215 nm), buffer A: H₂O/TFA (1:0.05% v/v), buffer B: CH₃CN/H₂O/TFA (4:1:0.05% v/v/v), gradient: buffer B (0 to 20% over 5 min then 20 to 42% over 60 min, 6 mL/min)) 15 mg of peptide 4 is obtained (Yield 24%).

LC-MS Analysis, RP-HPLC Chromatogram of Peptide 4
LC-MS: Buffer A: H₂O/TFA (1/0.1% v/v), Buffer B: CH₃CN/H₂O/TFA (4/1:0.1% v/v/v).

RP-HPLC on an XBridge BEH C18 column (300 Å, 3.5 μm, 4.6×150 mm) using a linear gradient 0-100% B over 30 minutes, flow rate 1 mL/min, UV detection (λ=215 nm).

MS: Electrospray ionization positive mode, voltage cone 30V, quadripolar analyser.

Figure 5A:
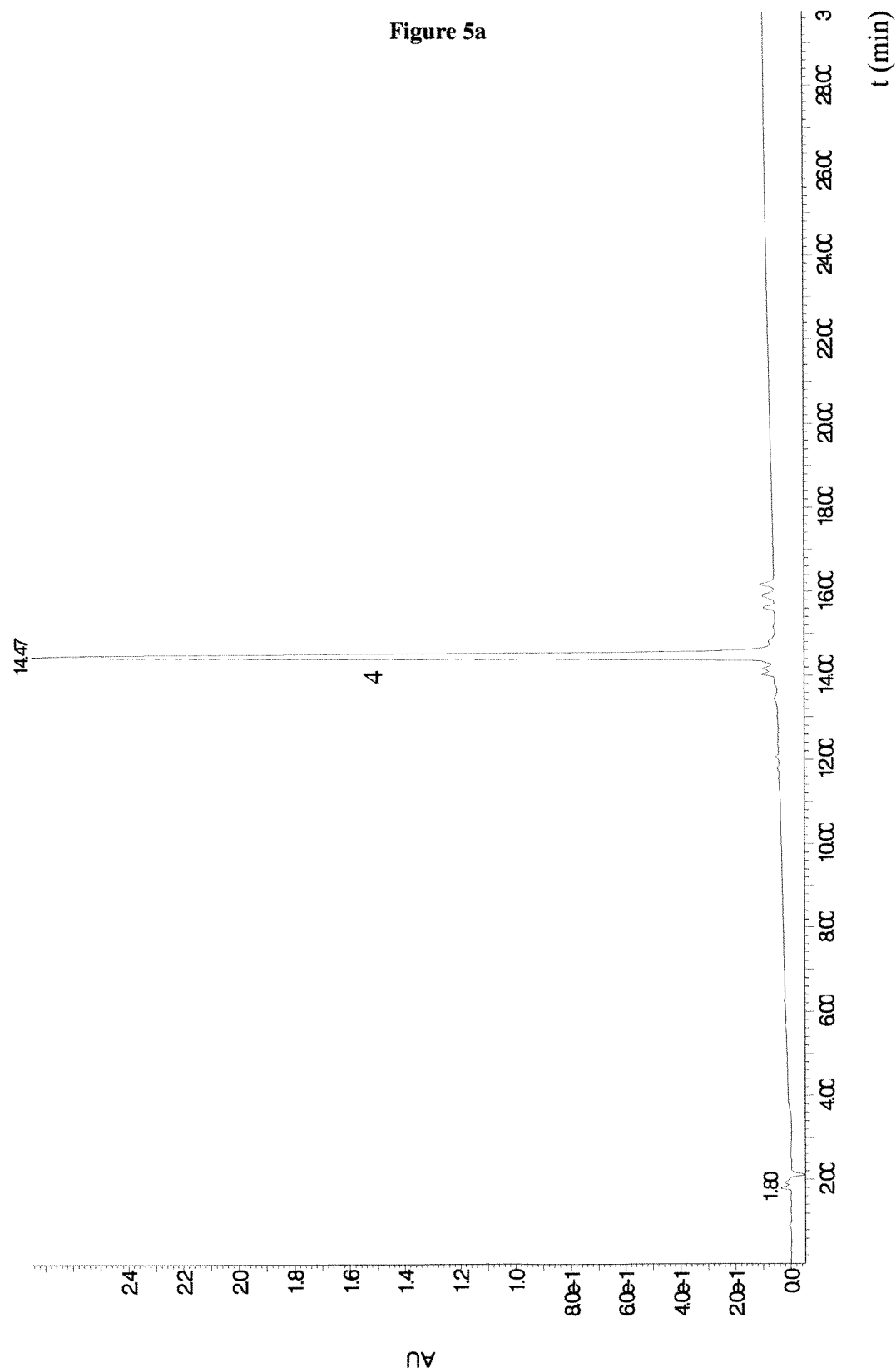
FIGS. 5a and 5b represent respectively the HPLC chromatogram and the mass spectrum of a functionalized peptide according to the invention after purification.
Figure 5B:
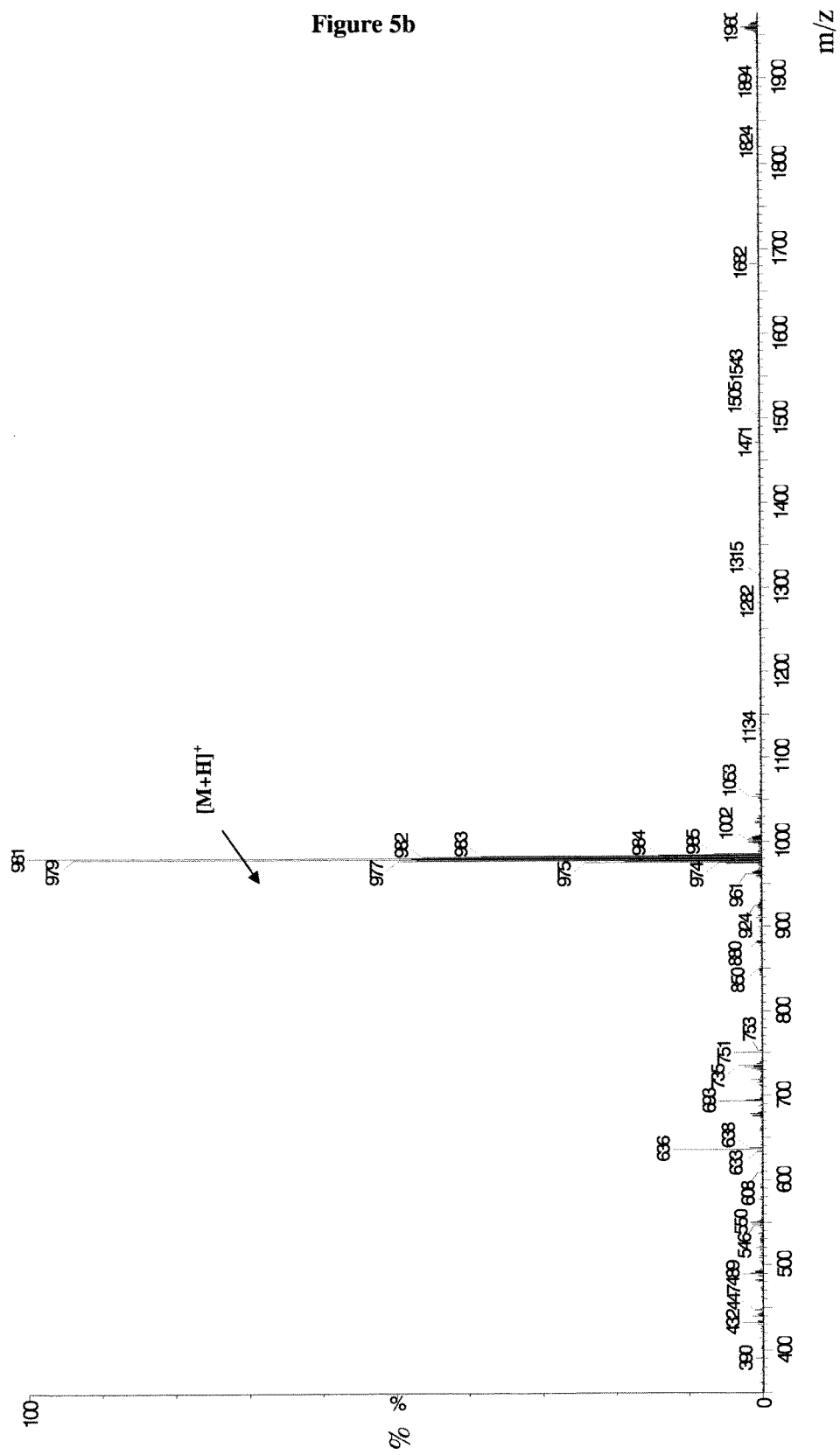

FIGS. 5a and 5b represent respectively the chromatogram and the mass spectrum of peptide 4 after purification.

Synthesis of Peptide 5: Ac-GFGQGFGG-SEA
The method for the synthesis of this peptide is described in the document Ollivier, N.; Dheur, J.; Mhidia, R.; Blanpain, A.; Melnyk, O. *Organic letters* 2010, 12, 5238-41.

Synthesis of Peptide 6, SEQ ID NO: 2 H-CILKEPVHGA-NH₂
The method for the synthesis of this peptide is described in the document Ollivier, N.; Dheur, J.; Mhidia, R.; Blanpain, A.; Melnyk, O. *Organic letters* 2010, 12, 5238-41.

Synthesis of Peptide 7, SEQ ID NO: 3 Ac-GFGQGFG-GCILKEPVHGA-NH₂ by SeEA Ligation. Comparison of the Reactivity of Peptide 4 Ac-GFGQGFGG-SeEA and Peptide 5 Ac-GFGQGFGG-SEA

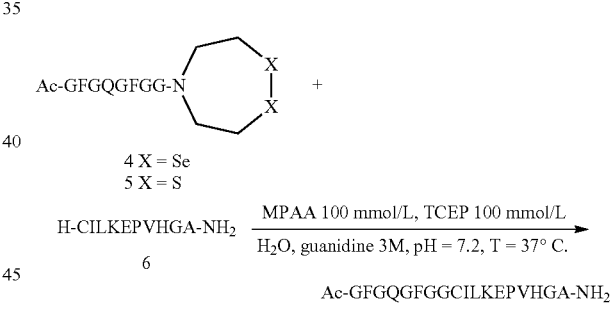

a—Ligation kinetics and yield of peptide 4 Ac-GFGQG-FGG-SeEA with peptide 6 H-CILKEPVHGA-NH₂

The SeEA ligation of peptide 4 with peptide 6 is carried out in a glove box (dioxygen concentration less than 50 ppm) under a nitrogen atmosphere. A 3M solution of guanidine is prepared in a 0.2M phosphate buffer at pH=7.3. Tris(2-carboxyethyl)phosphine (TCEP, 28.6 mg, 0.1 mmol) and 3-mercaptophenylacetic acid (MPAA, 16.8 mg, 0.1 mmol) are then added. The pH of the TCEP/MPAA/Guanidine solution obtained is adjusted to pH=7.2.

Peptides 4 (4.9 mg, 5 μmol) and 6 (10.6 mg, 7.6 μmol, 1.5 eq) are dissolved in the above TCEP/MPAA/Guanidine solution (1.5 mL). The reaction medium is stirred for 24 hours at 37° C.

Once the ligation reaction is completed, the reaction medium is diluted with water V=3 mL then acidified with a solution of TFA (10%) V=1 mL then the MPAA is extracted with ether using 3 times 6.5 mL.

The ligation product 7 in aqueous phase is purified directly by reversed-phase high-performance liquid chromatography (RP-HPLC) (C18 Nucleosil column (d=1 cm, L=20 cm, 120 Å, 5 µm), UV detection (λ=215 nm), buffer A: H₂O/TFA (1:0.05% v/v), buffer B: CH₃CN/H₂O/TFA (4:1:0.05% v/v/v), gradient: buffer B (0 to 20% over 5 min then 20 to 42% over 60 min, 6 mL/min). 5.6 mg of peptide 7 is obtained (Yield 54%).

LC-MS Analysis, RP-HPLC Chromatogram of Peptide 7

LC-MS: Buffer A: H₂O/TFA (1/0.1% v/v), Buffer B: CH₃CN/H₂O/TFA (4/1:0.1% v/v/v).

RP-HPLC on an XBridge BEH C18 column (300 Å, 3.5 µm, 4.6×150 mm) using a linear gradient 0-100% B over 30 minutes, flow rate 1 mL/min, UV detection (λ=215 nm).

MS: Electrospray ionization positive mode, voltage cone 30V, quadripolar analyser.

Figure 6A:
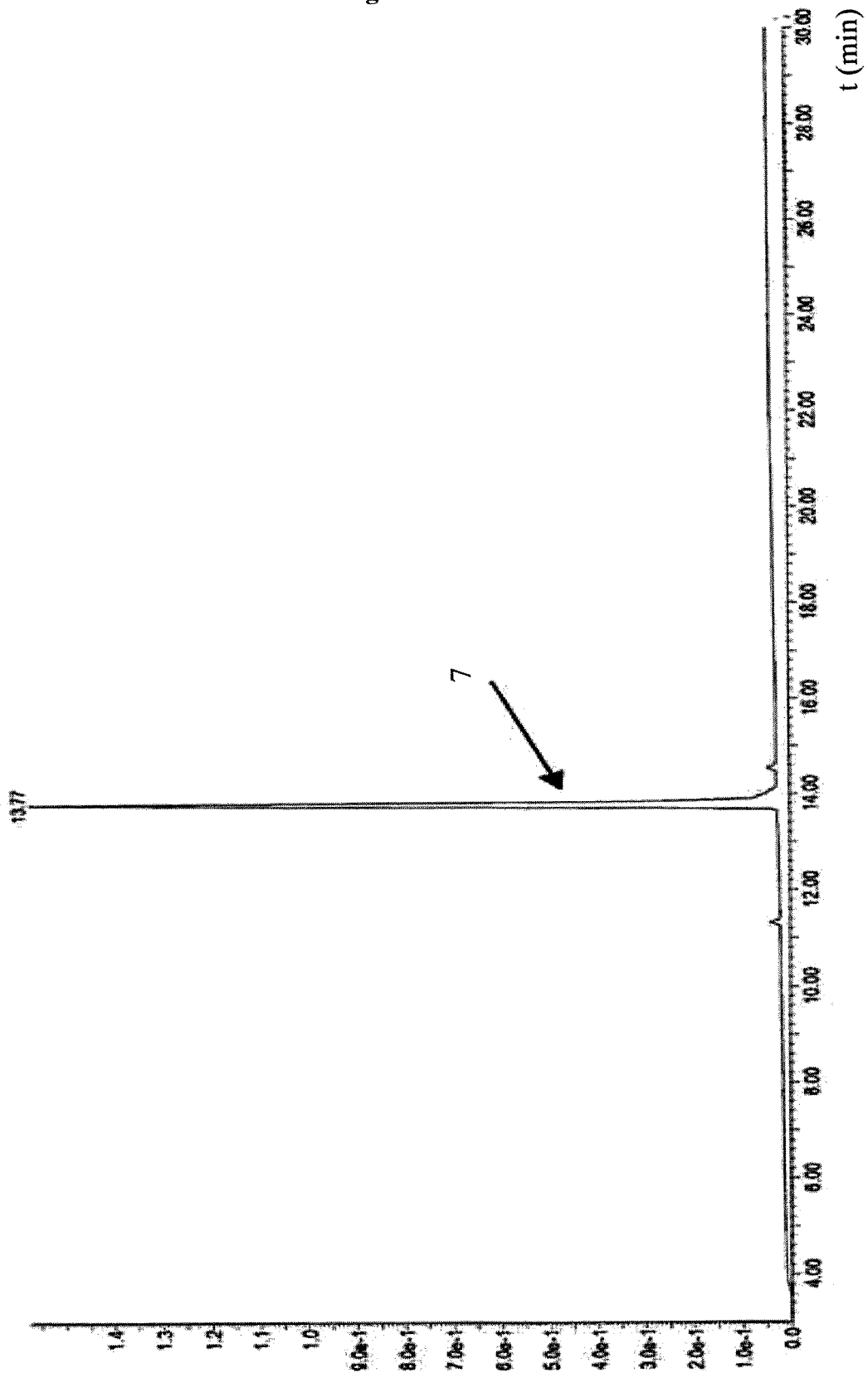
FIGS. 6a and 6b represent respectively the HPLC chromatogram and the mass spectrum of a polypeptide obtained by a ligation process according to the invention.
Figure 6B:
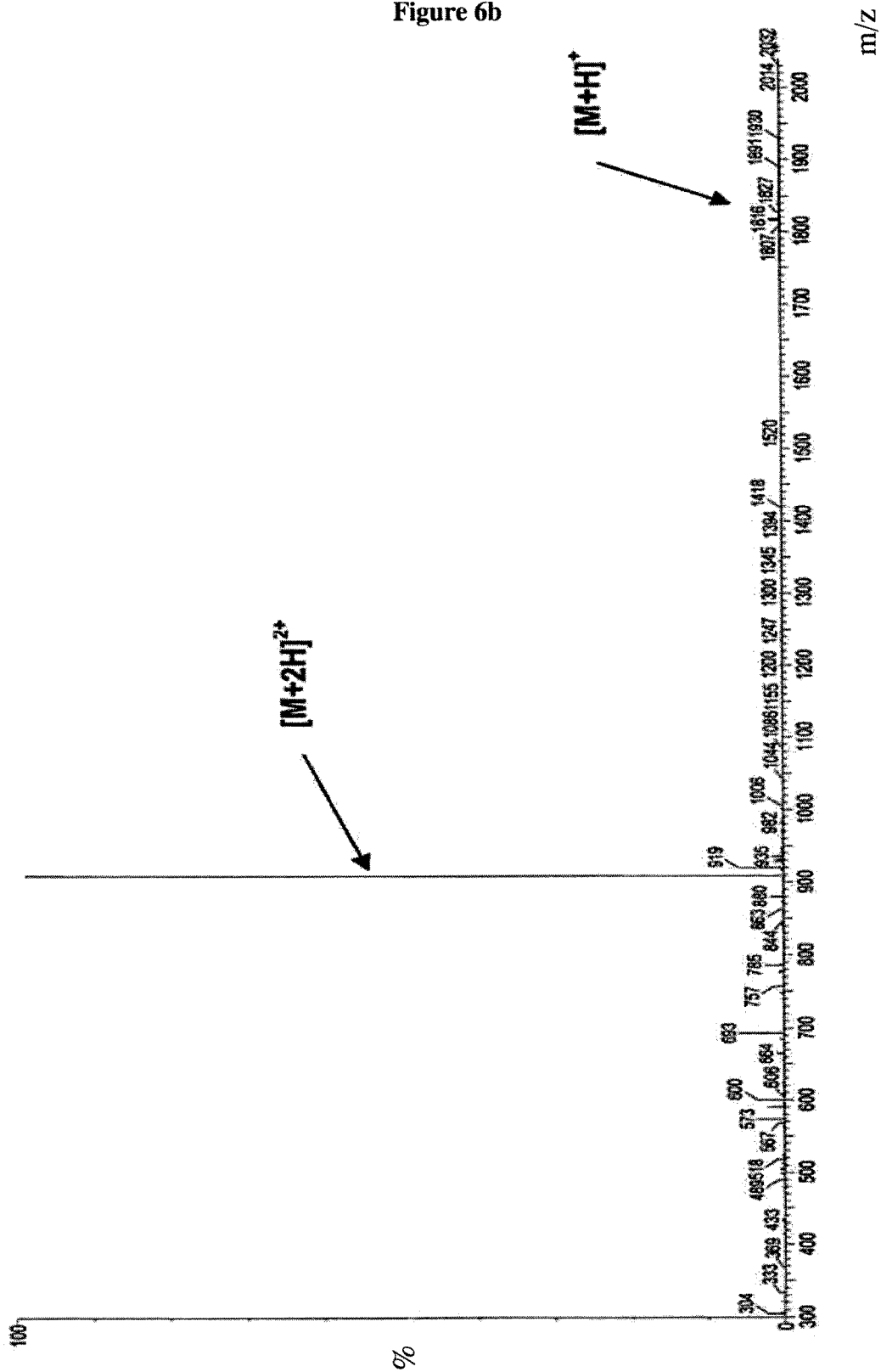

FIGS. 6a and 6b represent respectively the chromatogram and the mass spectrum of peptide 7 after purification.

b—Kinetics of the ligation of peptide 5 Ac-GFGQGFGG-SEA with peptide 6 H-CILKEPVHGA-NH₂

The reaction of SEA ligation of peptide 5 with peptide 6 is carried out under strictly the same conditions.

Comparison of the Kinetics

Figure 7:
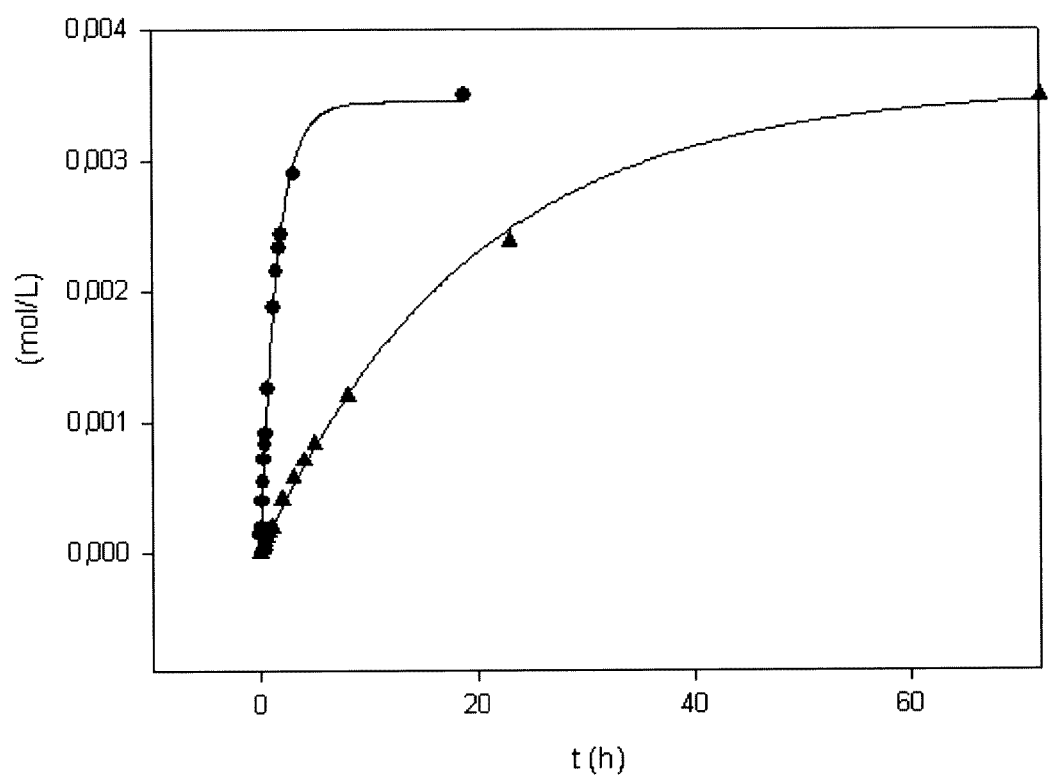
FIG. 7 represents a diagram measuring the reaction kinetics of a ligation process according to the invention and according to the prior art.

FIG. 7 represents a comparison of the kinetics of the ligation reaction for the formation of peptide 7, with a selenium-based compound (peptide 4) according to the invention, curve represented by the symbol ● or with a sulphur-based compound (peptide 5) according to the state of the art, curve represented by the symbol ▲.

FIG. 7 shows a higher reaction rate for the ligation reaction according to the invention, curve represented by the symbol ●.

Example 4

Comparison of the Ligation Kinetics for the SeEA, SEA and NCL (Thioester Chemistry) Methods Synthesis of Peptide 15a: H-ILKEPVHGV-SEA The method for the synthesis of this peptide is described in the document Ollivier, N.; Dheur, J.; Mhidia, R.; Blanpain, A.; Melnyk, O. *Organic letters* 2010, 12, 5238-41.

Synthesis of Peptide 15b: H-ILKEPVHGV-SeEA

Starting from peptide 15a, the method for the synthesis of peptide 15b is strictly identical to that used for the synthesis of peptide 9.

Synthesis of Peptide 15c: H-ILKEPVHGV-MPA (MPA=3-mercapto propionic acid)

The method for the synthesis of this peptide is described in the document Dheur, J.; Ollivier, N.; Vallin, A.; Melnyk, O. *Journal of Organic Chemistry* 2010, 76, 3194-3202.

Comparison of the Ligation Kinetics of Peptide 15a/15b/15c H-ILKEPVHGV-R with Peptide 6 H-CILKEPVHGA-NH₂ for the SeEA, SEA Ligation and NCL Methods

H-ILKEPVHGV-R +
15

H-CILKEPVHGA-NH₂ $\xrightarrow[\text{H}_2\text{O, pH} = 7.2, \text{T} = 37°\text{C.}]{\text{TCEP 200 mmol/L,} \atop \text{MPAA 200 mmol/L}}$
6

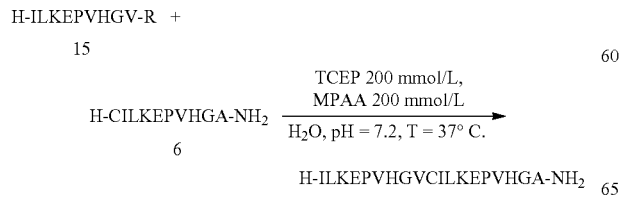

H-ILKEPVHGVCILKEPVHGA-NH₂
16

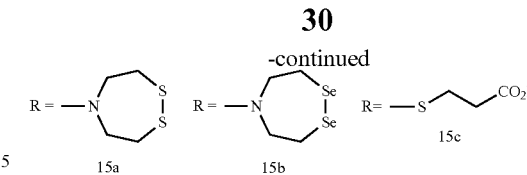

The different ligations of peptide 15a or 15b or 15c with peptide 6 are carried out separately in a glove box ([O₂]<50 ppm) under a nitrogen atmosphere. A 200 mmol/L solution of TCEP is prepared in a 0.1M phosphate buffer at pH=7.2. 3-Mercaptophenylacetic acid (MPAA 33 mg, 0.2 mmol) is then added. The pH of the TCEP/MPAA solution obtained is adjusted to pH=7.2.

Peptides 15a or 15b or 15c and 6 (1.5 eq) are dissolved separately in the above TCEP/MPAA solution at a concentration of 3 mmol/L. The reaction medium is stirred for 24 hours at 37° C. The formation kinetics of ligation product 16 are monitored by HPLC.

Figure 12:
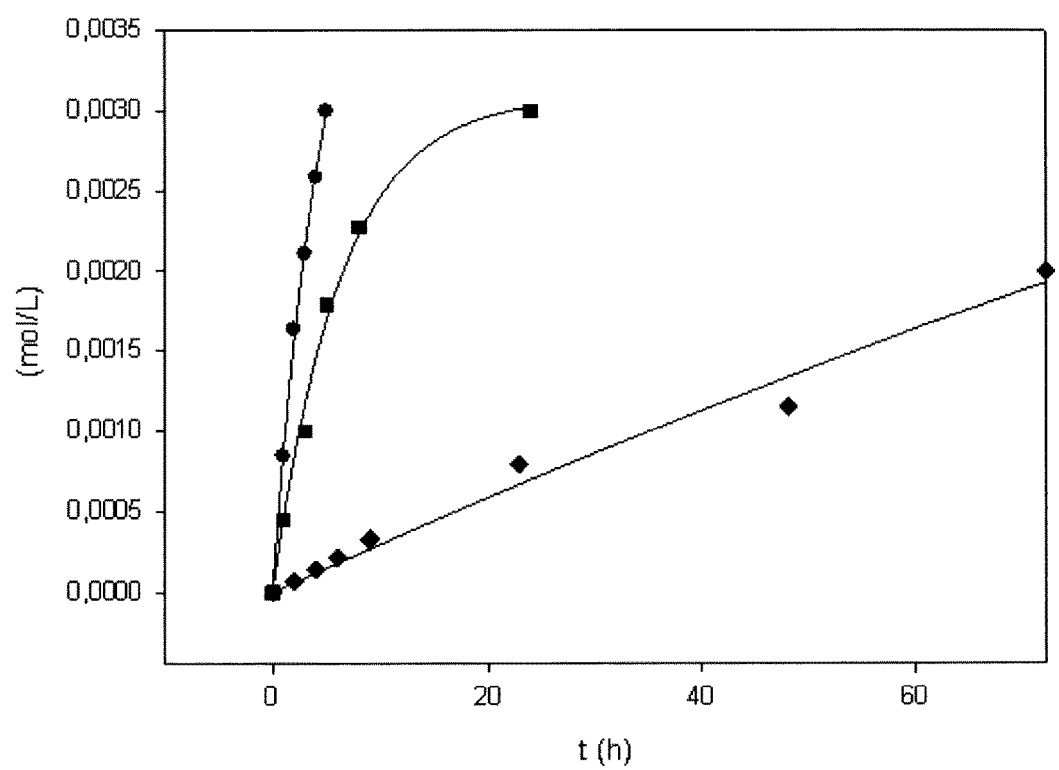
FIG. 12 represents a diagram measuring the reaction kinetics of a ligation process according to the invention and according to the prior art.

FIG. 12 allows comparison of the formation reaction kinetics of peptide 16 according to the SeEA, SEA ligation or NCL (thioester chemistry) method.

In FIG. 12, the curve represented by ● corresponds to the formation of peptide 16 from peptide 15b, the curve represented by ■ corresponds to the formation of peptide 16 from peptide 15a and the curve represented by ♦ corresponds to the formation of peptide 16 from peptide 15c.

FIG. 12 shows an SeEA ligation reaction rate (curve represented by ●) higher than that of the NCL method (curve represented by ■), itself significantly higher than that of the SEA method (curve represented by ♦).

Example 5

Formation of SeEA Segments In Situ by Simultaneous Exchange and Ligation—Catalysis of the Ligation Reaction 11-Synthesis of Peptide 10: H-ILKEPVHGY-SEA The method for the synthesis of this peptide is described in the document Ollivier, N.; Dheur, J.; Mhidia, R.; Blanpain, A.; Melnyk, O. *Organic letters* 2010, 12, 5238-41.

a—Ligation kinetics of peptide 10 H-ILKEPVHGY-SEA with peptide 6 H-CILKEPVHGA-NH₂ in the presence of Se₃EA linker 2 in order to produce peptide 11, SEQ ID NO: 4 H-ILKEPVHGYCILKEPVHGA-NH₂

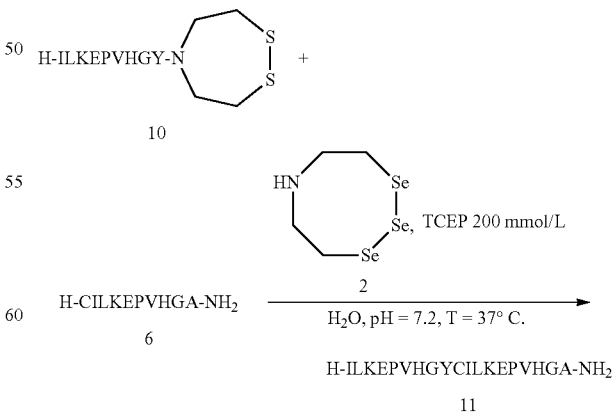

The SEA ligation of peptide 10 with peptide 6 is carried out in a glove box (dioxygen concentration less than 50 ppm) under a nitrogen atmosphere. A 200 mmol/L solution of TCEP is prepared in a 0.1 M phosphate buffer at pH 7.2.

Peptides 10 (1 mg, 0.6 μmol) and 6 (1.4 mg, 1 μmol, 1.5 eq) as well as the Se₃EA linker 2 (5.8 mg, 0.02 mmol, 28 eq) are dissolved in the above solution of TCEP (94 μL). The reaction medium is stirred for 24 hours at 37° C. The ligation formation kinetics of product 11 are monitored by HPLC.

b—Comparison of the ligation kinetics of peptide 10 H-ILKEPVHGY-SEA with peptide 6 H-CILKEPVHGA-NH₂ in the presence of MPAA

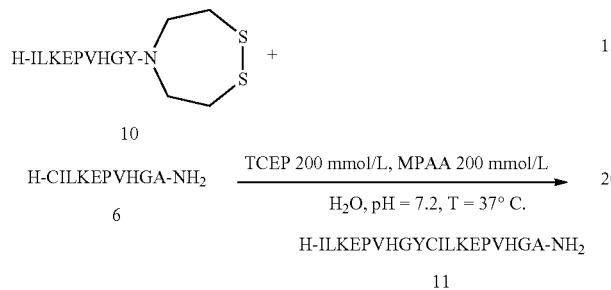

The SEA ligation of peptide 10 with peptide 6 is carried out in a glove box (dioxygen concentration less than 50 ppm) under a nitrogen atmosphere. A 200 mmol/L solution of TCEP is prepared in a 0.1M phosphate buffer at pH 7.2. 3-Mercaptophenylacetic acid (MPAA 33 mg, 0.2 mmol) is then added. The pH of the TCEP/MPAA solution obtained is adjusted to pH=7.2.

Peptides 10 (1 mg, 5 μmol) and 6 (10.6 mg, 7.6 μmol, 1.5 eq) are dissolved in the above TCEP/MPAA solution (94 μL). The reaction medium is stirred for 24 hours at 37° C. The formation kinetics of ligation product 11 are monitored by HPLC.

Figure 8:
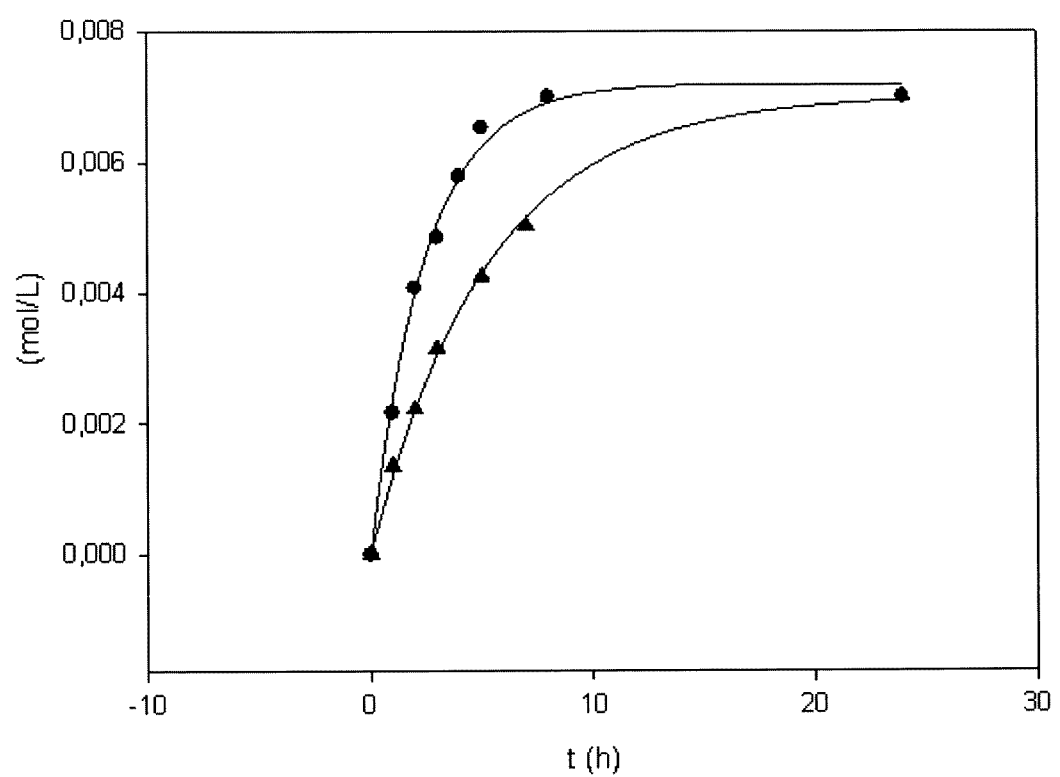
FIG. 8 represents a diagram measuring the reaction kinetics of a ligation process according to the invention and according to the prior art.

FIG. 8 allows comparison of the reaction kinetics of the formation of peptide 11 in the presence or not of compound 2 according to the invention.

In FIG. 8, the curve represented by ● corresponds to the ligation according to the invention of peptide 10 in the presence of selenium-containing compound 2 and the curve represented by ▲ corresponds to the ligation according to the prior art of peptide 10 without the selenium-containing compound but in the presence of MPAA.

FIG. 8 shows a higher reaction rate when compound 2 is present.

Example 6

One-pot Sequential Ligation of Three Segments Using SeEA and SEA Ligations

Synthesis of Peptide 12: H—C(StBu)HHLEPGG-SEA

The method for the synthesis of this peptide is described in the document Ollivier, N.; Dheur, J.; Mhidia, R.; Blanpain, A.; Melnyk, O. *Organic letters* 2010, 12, 5238-41.

Synthesis of Peptide 14, SEQ ID NO: 5 Ac-GFGQGFGG-CHHLEPGG-CILKEPVHGA-NH₂ by Ligation of Segments 4 Ac-GFGQGFGG-SeEA, 12 H—C(StBu)HHLEPGG-SEA and 6 H-CILKEPVHGA-NH₂

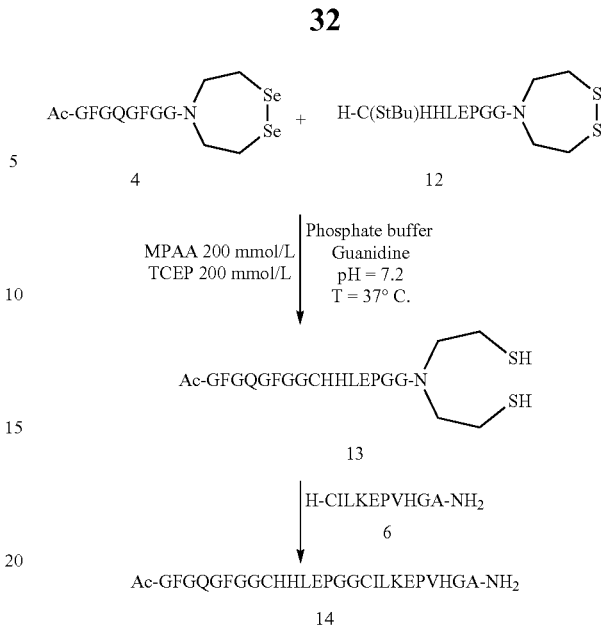

—Step 1

Guanidine hydrochloride (GdnHCl, 573.18 mg, 6 mmol) is dissolved in 0.1 M phosphate buffer pH=7.3 (1 mL final, 6M).

4-Mercaptophenylacetic acid (MPAA, 33.83 mg, 0.2 mmol) and tris(2-carboxyethyl)phosphine hydrochloride (TCEP-HCl, 57.37 mg, 0.2 mmol) are dissolved in this solution (1 mL). 6M NaOH is added to adjust the pH of the solution to 7.37.

Peptides 4 Ac-GFGQGFGG-SeEA (5.33 mg, 5.4 μmol) and 12 H—C(StBu)HHLEPGG-SEA (7.59 mg, 5.4 μmol) are dissolved together in the above solution (780 μL). The reaction medium is placed in a thermostatically controlled bath at 37° C. under an inert atmosphere.

The ligation is monitored by RP-HPLC on an XBridge BEH C18 column (4.6×250 mm, 300 Å, 5 μm) (215 nm, 1 mL/min, 30° C., buffer A water containing 0.1% TFA, buffer B CH₃CN/water 4/1 containing 0.1% TFA, 0-100% B over 30 min). For this, an aliquot (2 μL) of reaction medium is acidified with 10% aqueous TFA, extracted with Et₂O in order to remove MPAA before analysis.

Peptide 13 Ac-GFGQGFGG-CHHLEPGG-SEA in solution is obtained in this way.

Figure 9A:
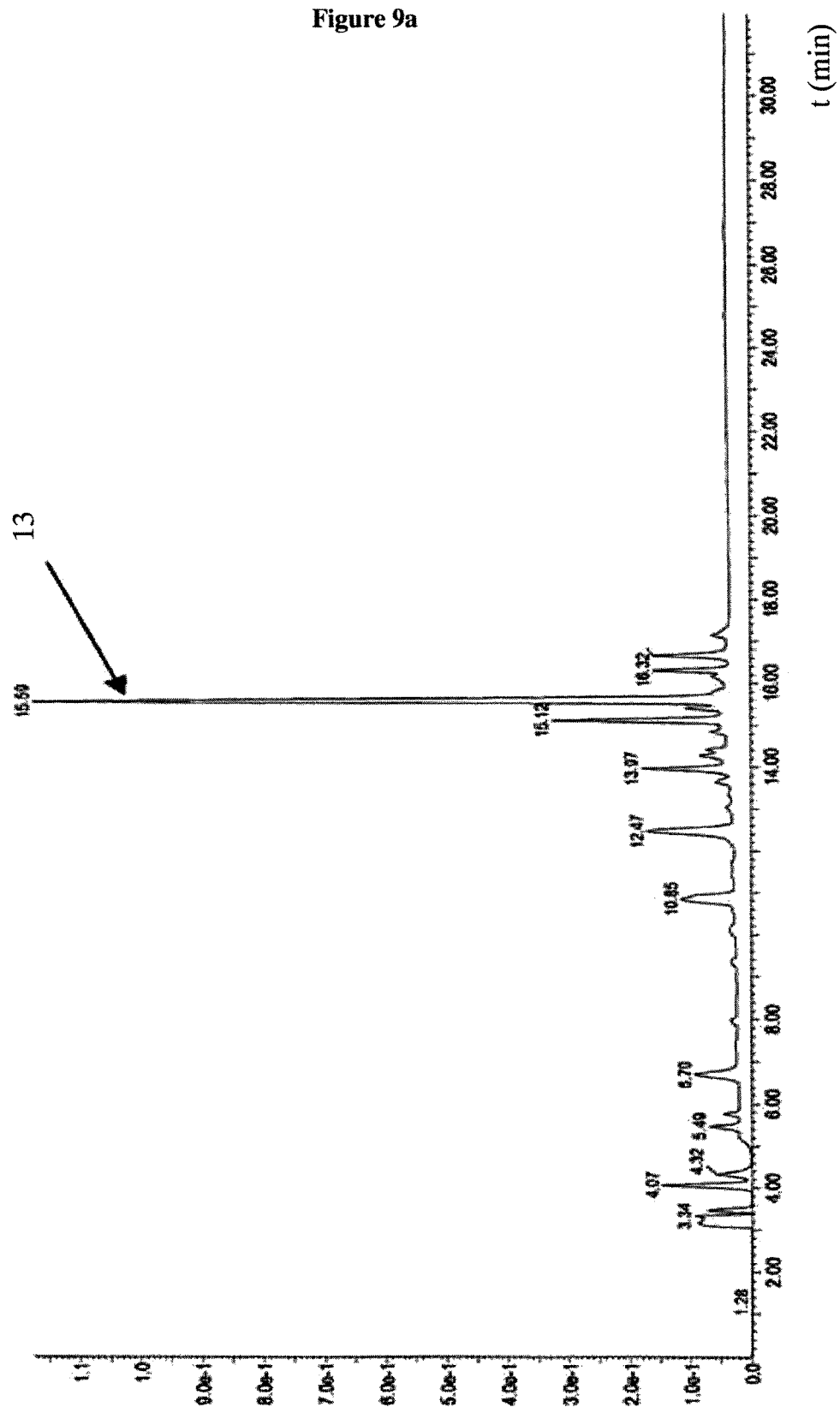
FIGS. 9a and 9b represent respectively the HPLC chromatogram and the mass spectrum of a functionalized polypeptide obtained by a process according to the invention.
Figure 9B:
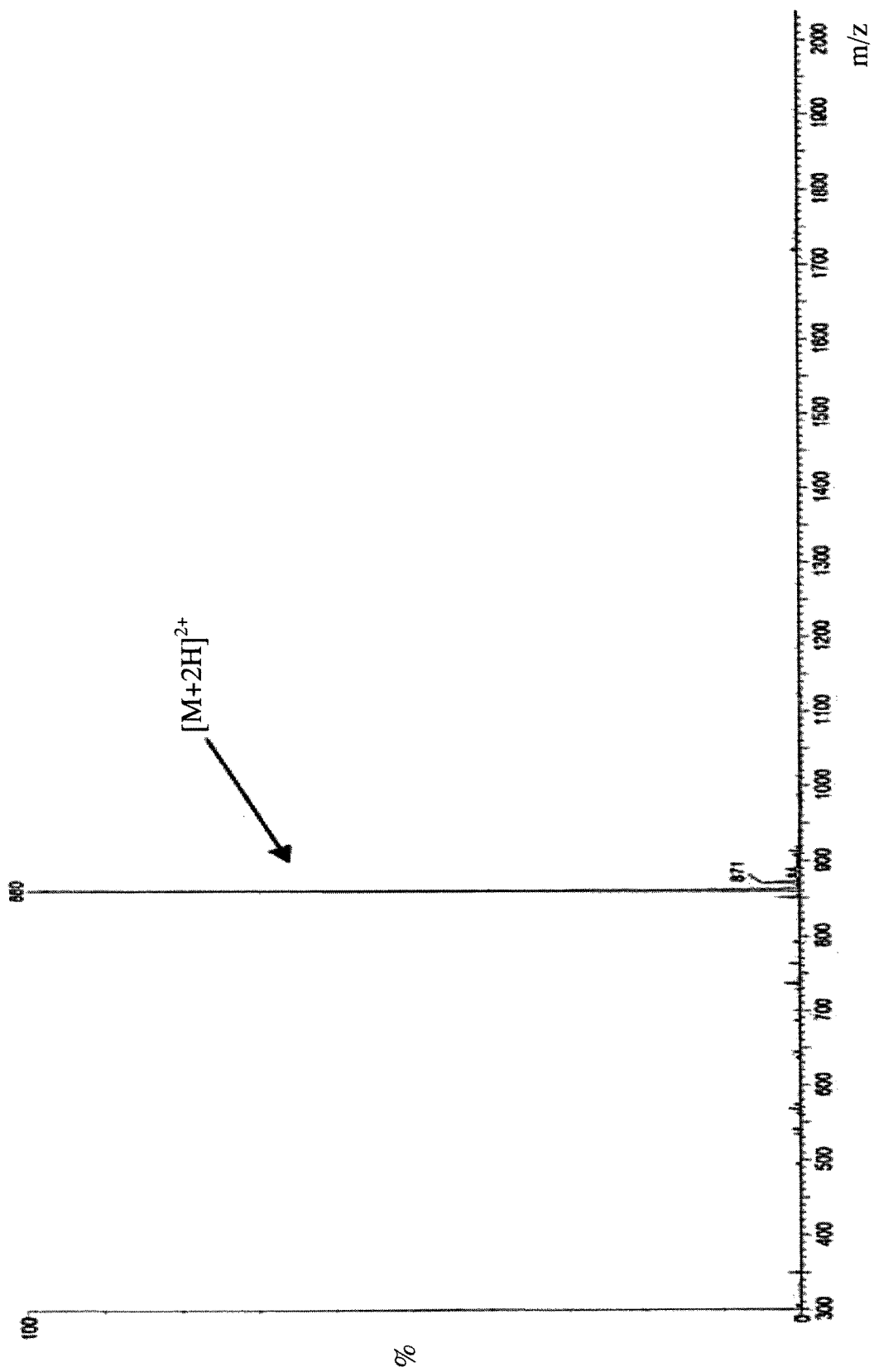

FIGS. 9a and 9b represent respectively the chromatogram and the mass spectrum of peptide 13.

—Step 2

After reaction for 4 hours 35 minutes, peptide 6 H-CILKEPVHGA-NH₂ (11.06 mg, 8.1 μmol) is added in solid form to the reaction medium. The reaction is placed under an inert atmosphere at 37° C.

The ligation is monitored by RP-HPLC on an XBridge BEH C18 column (4.6×250 mm, 300 Å, 5 μm) (215 nm, 1 mL/min, 30° C., buffer A water containing 0.1% TFA, buffer B CH₃CN/water 4/1 containing 0.1% TFA, 0-100% B over 30 min). For this, an aliquot (2 μL) of reaction medium is acidified with 10% aqueous TFA, extracted with Et₂O in order to remove MPAA before analysis.

When the reaction is complete, the reaction medium is diluted with water (4 mL) and 10% aqueous TFA (1 mL) is added. After 4 extractions with Et₂O (4×4 mL), the aqueous phase is degassed for 2 minutes by bubbling argon through it. After purification by RP-HPLC on a nucleosil C18 column, 120 Å, 5 μm (215 nm, 6 mL/min, buffer A water containing 0.05% TFA, buffer B CH3CN/water 4/1 containing 0.05% TFA, 0-10% B over 5 min, then 10-100% B over 150 min), 6 mg (36%) of peptide 14 Ac-GFGQGFGG-CHHLEPGG-CILKEPVHGA-NH₂ is obtained.

Figure 10A:
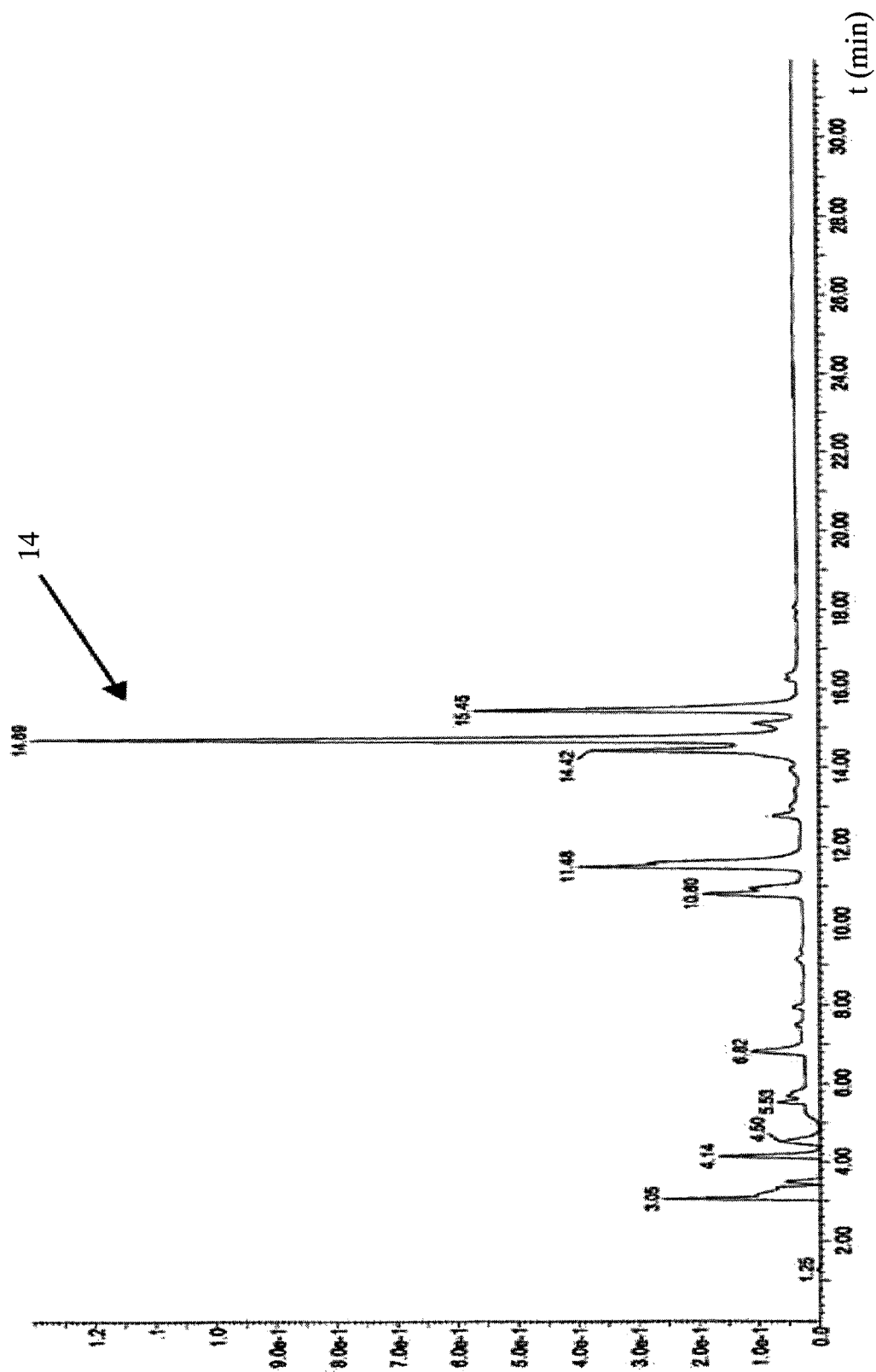
FIGS. 10a and 10b represent respectively the chromatogram and the mass spectrum of a polypeptide obtained by a process according to the invention.
Figure 10B:
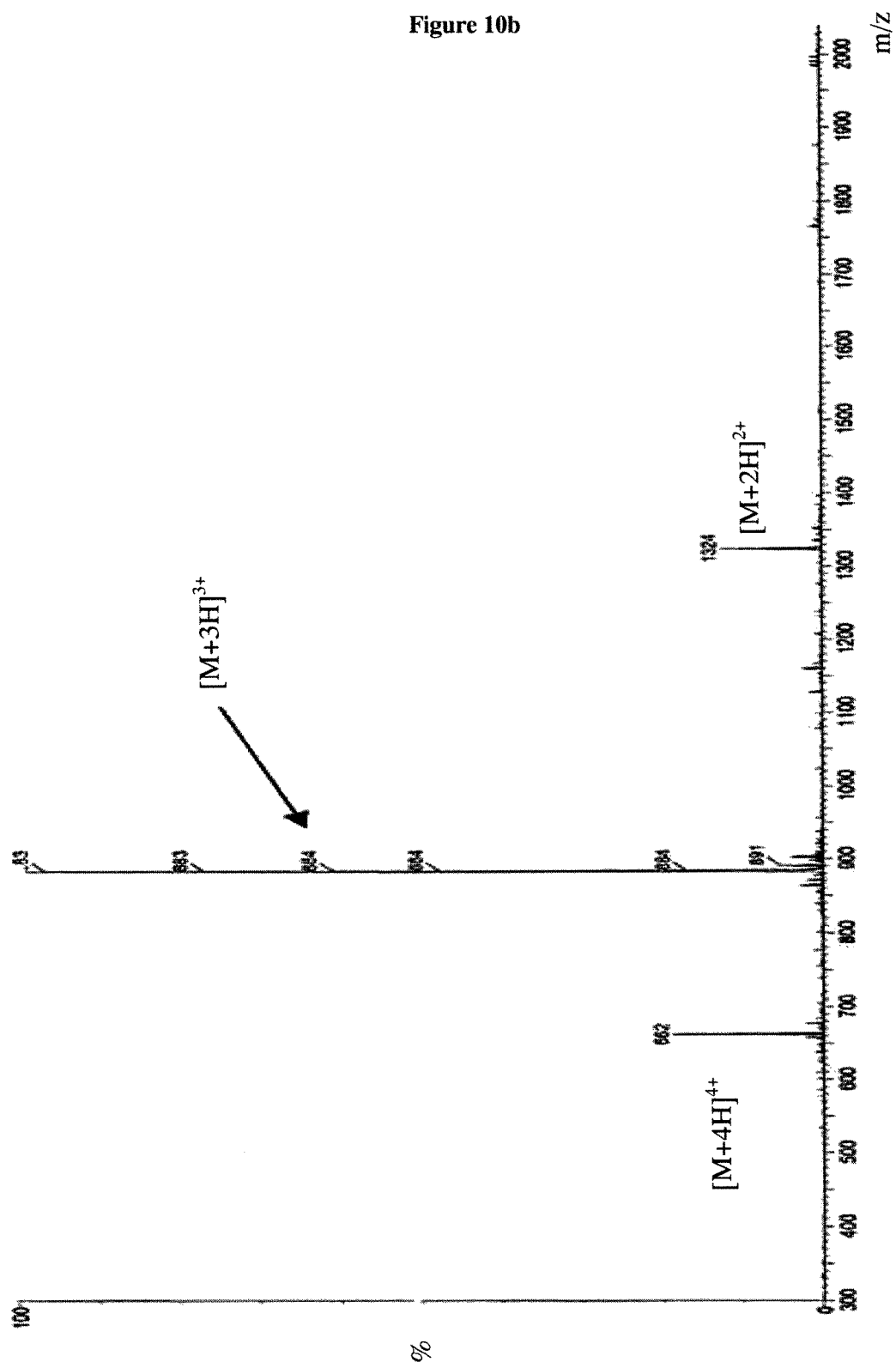

FIGS. 10a and 10b represent the chromatogram and the mass spectrum of compound 14 before purification respectively.

Figure 11A:
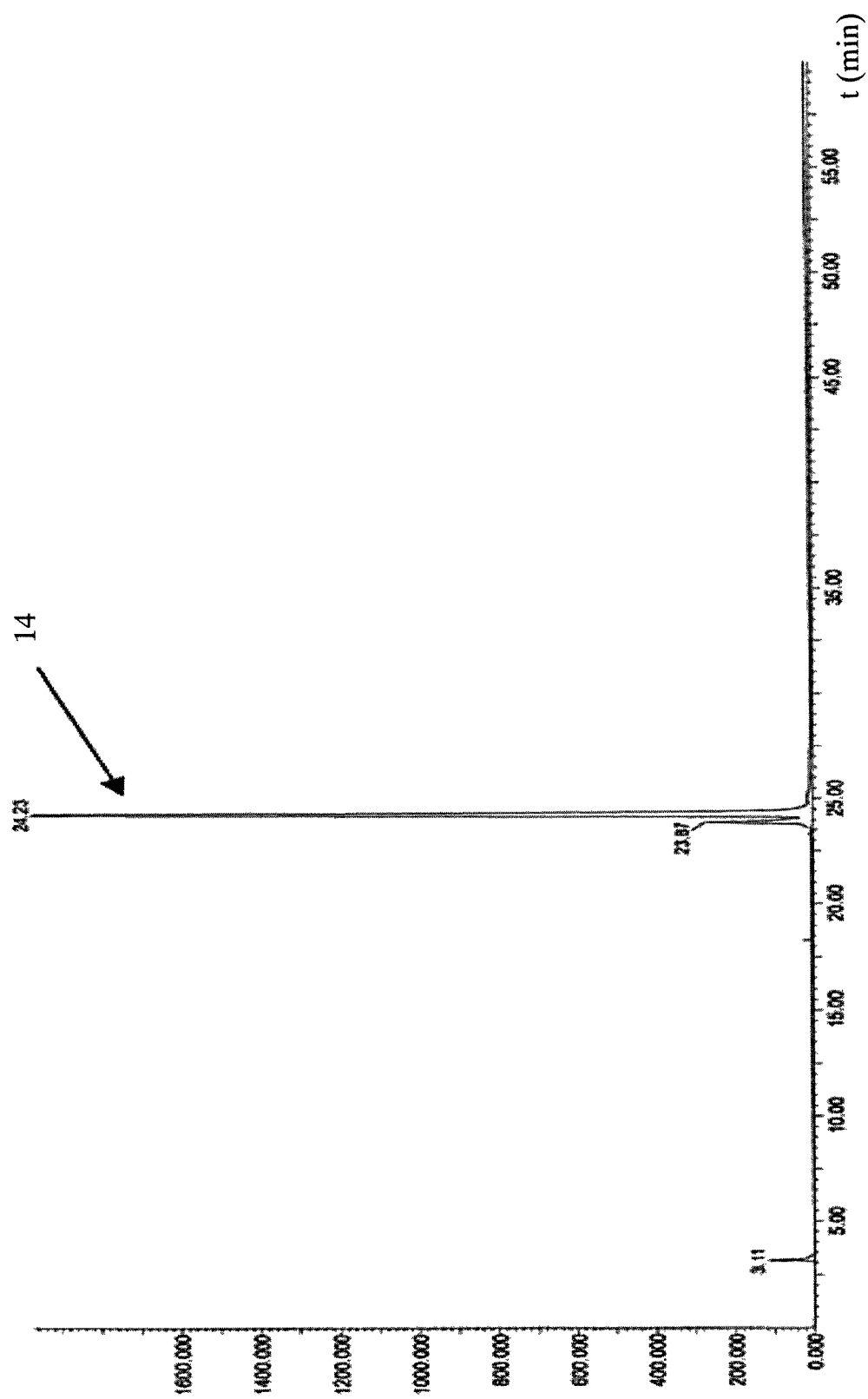
FIGS. 11a and 11b represent respectively the chromatogram and the mass spectrum of a polypeptide obtained by a process according to the invention after purification.
Figure 11B:
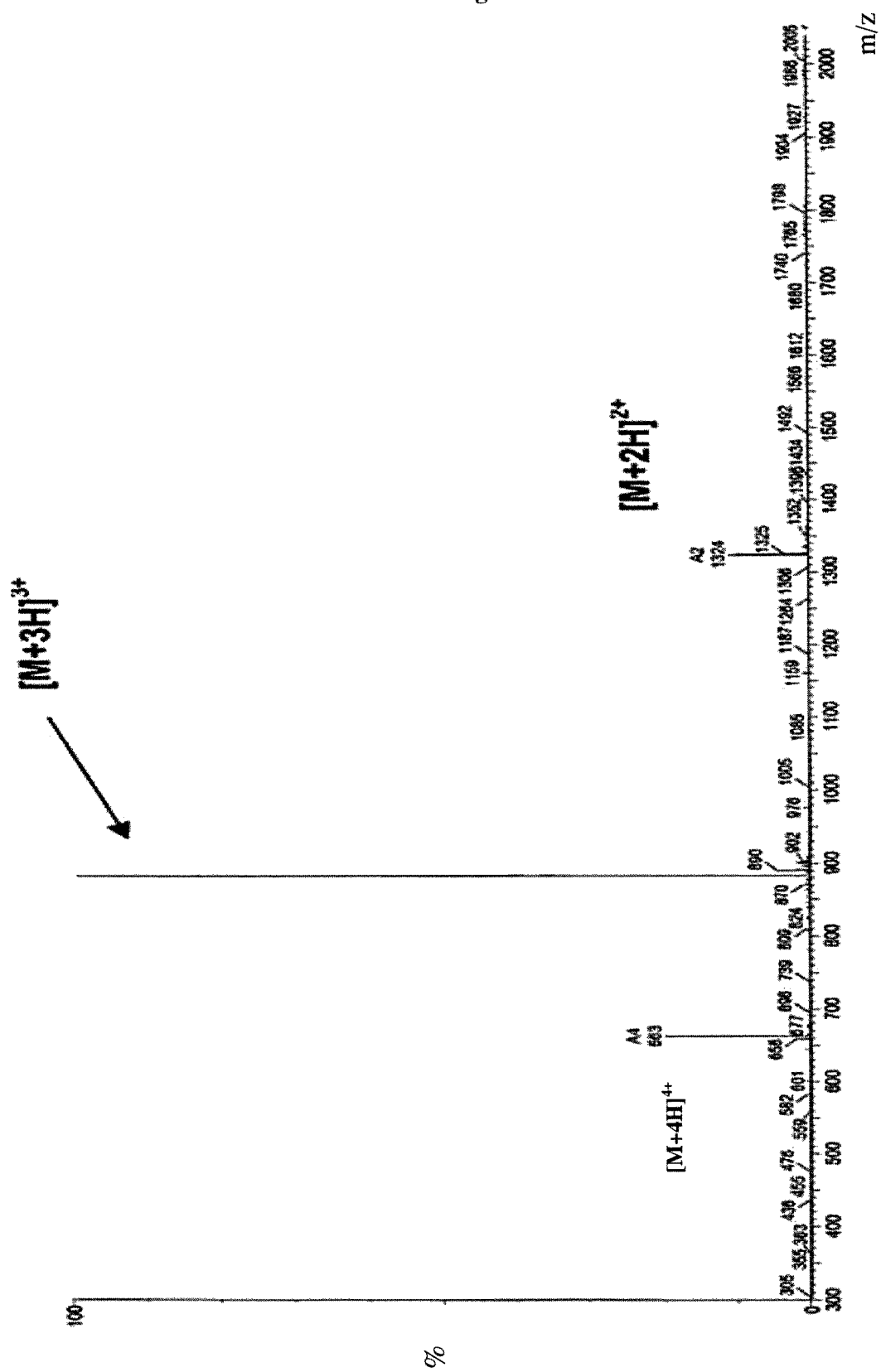

FIGS. 11a and 11b represent the chromatogram and the mass spectrum of compound 14 after purification respectively.

The invention claimed is:

1. A functionalized peptide selected from:
a) the peptide of formula (I): $X_1$—$N(CH_2CH_2SeH)_2$; or
b) the peptide of formula (I'):

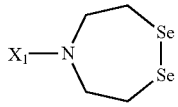

in which $X_1$ represents a peptide fragment and the —$N(CH_2CH_2SeH)_2$ group or

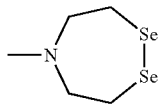

group forms an amide bond with the C=O termination of the amino acid residue of the peptide fragment $X_1$ which is in the C-terminal position.

2. The functionalized peptide according to claim 1, in which $X_1$ comprises from 2 to 300 amino acid residues.

3. A compound selected from:
a) the compound of formula (III'):

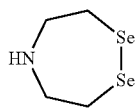

b) the compound of formula (III''):

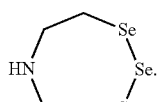

4. A functionalized polymer resin, with the structure (V):

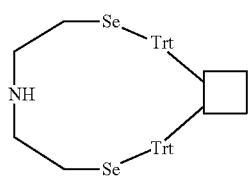

Or the structure (V'):

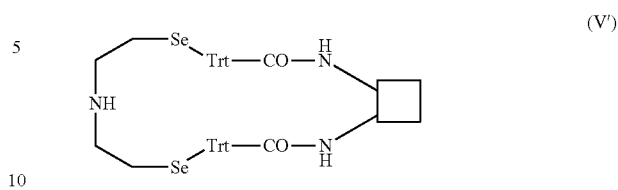

in which, □ represents a solid support, Trt represents a triphenylmethyl group optionally substituted by one or more substituents, $X_1$ represents a peptide fragment.

5. A polymer resin comprising a peptide fragment corresponding to formula (VII) or (VII'):

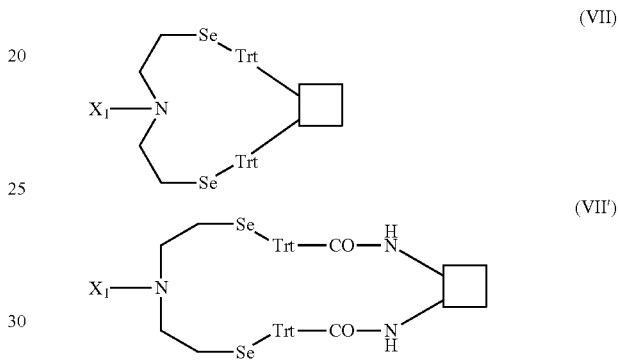

in which, □ represents a solid support, Trt represents a triphenylmethyl group optionally substituted by one or more substituents, $X_1$ represents a peptide fragment.

6. The polymer resin according to claim 4, in which the solid support □ is selected from the group consisting of a polystyrene, a polyacrylamide, a polyethylene glycol, a cellulose, a polyethylene, a polyester, a latex, a polyamide, a polydimethylacrylamide, a polyethylene glycol-polystyrene copolymer, a polyethylene glycol-polyacrylamide copolymer and derivatives thereof.

7. The polymer resin according to claim 5, in which the solid support □ is selected from the group consisting of a polystyrene, a polyacrylamide, a polyethylene glycol, a cellulose, a polyethylene, a polyester, a latex, a polyamide, a polydimethylacrylamide, a polyethylene glycol-polystyrene copolymer, a polyethylene glycol-polyacrylamide copolymer and derivatives thereof.

8. A polypeptide synthesis kit comprising at least one compound according to claim 3.

9. The functionalized peptide according to claim 2, in which $X_1$ comprises from 5 to 100 amino acid residues.

10. The functionalized peptide according to claim 2, in which $X_1$ comprises from 8 to 50 amino acid residues.

11. The functionalized peptide according to claim 4, wherein the triphenylmethyl group is substituted by one or more substituents selected from group consisting of chlorine, methoxy, methyl, fluorine and cyano.

12. The functionalized peptide according to claim 5, wherein the triphenylmethyl group is substituted by one or more substituents selected from group consisting of chlorine, methoxy, methyl, fluorine and cyano.

* * * * *

```
                          SEQUENCE LISTING

<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: PEPTIDE 3 ACETYL

<400> SEQUENCE: 1

Gly Phe Gly Gln Gly Phe Gly Gly
1               5

<210> SEQ ID NO 2
<211> LENGTH: 10
<212> TYPE: PRT
<213> ORGANISM: Artificial Sequence
<220> FEATURE:
<223> OTHER INFORMATION: PEPTIDE 6

<400> SEQUENCE: 2

Cys Ile Leu Lys Glu Pro Val His Gly Ala
1               5                   10

<210> SEQ ID NO 3
<211> LENGTH: 18
<212> TYPE: PRT
<213> ORGANISM: Artificial Sequence
<220> FEATURE:
<223> OTHER INFORMATION: PEPTIDE 7 ACETYL

<400> SEQUENCE: 3

Gly Phe Gly Gln Gly Phe Gly Gly Cys Ile Leu Lys Glu Pro Val His
1               5                   10                  15

Gly Ala

<210> SEQ ID NO 4
<211> LENGTH: 19
<212> TYPE: PRT
<213> ORGANISM: Artificial Sequence
<220> FEATURE:
<223> OTHER INFORMATION: PEPTIDE 11

<400> SEQUENCE: 4

Ile Leu Lys Glu Pro Val His Gly Tyr Cys Ile Leu Lys Glu Pro Val
1               5                   10                  15

His Gly Ala

<210> SEQ ID NO 5
<211> LENGTH: 26
<212> TYPE: PRT
<213> ORGANISM: Artificial Sequence
<220> FEATURE:
<223> OTHER INFORMATION: PEPTIDE 14 ACETYL

<400> SEQUENCE: 5

Gly Phe Gly Gln Gly Phe Gly Gly Cys His His Leu Glu Pro Gly Gly
1               5                   10                  15

Cys Ile Leu Lys Glu Pro Val His Gly Ala
            20                  25
```